(12) United States Patent
McMahon et al.

(10) Patent No.: US 10,413,742 B2
(45) Date of Patent: *Sep. 17, 2019

(54) DEFIBRILLATOR PATIENT MONITORING POD

(71) Applicant: Physio-Control, Inc., Redmond, WA (US)

(72) Inventors: Michael D. McMahon, Forest Park, WA (US); Christopher Pearce, Monroe, WA (US); Peter Wung, Redmond, WA (US); John C. Daynes, Redmond, WA (US); Kenneth J. Peterson, Bellevue, WA (US); Maren L. Nelson, Kirkland, WA (US); James S. Neumiller, Redmond, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 369 days.

This patent is subject to a terminal disclaimer.

(21) Appl. No.: 14/069,021

(22) Filed: Oct. 31, 2013

(65) Prior Publication Data
US 2014/0142647 A1 May 22, 2014

Related U.S. Application Data

(62) Division of application No. 10/583,176, filed on Mar. 5, 2008, now Pat. No. 8,600,491.

(51) Int. Cl.
*A61N 1/39* (2006.01)

(52) U.S. Cl.
CPC .................. *A61N 1/3925* (2013.01)

(58) Field of Classification Search
CPC ....... A61N 1/046; A61N 1/3993; A61N 1/375
(Continued)

(56) References Cited

U.S. PATENT DOCUMENTS

| 3,724,455 A | 4/1973 | Unger et al. |
| 3,865,101 A | 2/1975 | Saper et al. |

(Continued)

FOREIGN PATENT DOCUMENTS

| EP | 0801959 | 10/1997 |
| EP | 0923961 | 6/1999 |

(Continued)

OTHER PUBLICATIONS

Notice of Allowance, dated Sep. 3, 2013, U.S. Appl. No. 10/583,176, filed Mar. 5, 2008.

(Continued)

*Primary Examiner* — Amanda K Hulbert
*Assistant Examiner* — Natasha Patel
(74) *Attorney, Agent, or Firm* — Lane Powell PC

(57) ABSTRACT

A patient parameter monitoring pod in embodiments of the teachings may include one or more of the following features: (a) portable housing containing a power supply, (b) a patient parameter module connectable to a patient via lead cables to collect patient data, the patient data including at least one vital sign, (c) a transceiver adapted to wirelessly transmit the patient data to a defibrillator, (d) a data port adapted to supply the patient data via a direct electrical connection to the defibrillator, and (e) a carrying handle extending from the housing proximate a patient lead cable port that permits connection of the lead cables to the pod, the carrying handle positioned to protect the patient lead cable port and the patient lead cables attached to the port from direct impact.

12 Claims, 19 Drawing Sheets

(58) Field of Classification Search
USPC ........................................................ 600/523
See application file for complete search history.

(56) References Cited

U.S. PATENT DOCUMENTS

| | | |
|---|---|---|
| 4,096,856 A | 6/1978 | Smith et al. |
| 4,635,639 A | 1/1987 | Hakala et al. |
| 4,916,439 A | 4/1990 | Estes et al. |
| 50,124,111 | 4/1991 | Policastro et al. |
| 5,078,134 A | 1/1992 | Heilman et al. |
| 5,105,821 A | 4/1992 | Reyes et al. |
| 5,311,449 A | 5/1994 | Adams et al. |
| 5,321,837 A | 6/1994 | Daniel et al. |
| 5,419,336 A | 5/1995 | Margison et al. |
| 5,470,343 A | 11/1995 | Fincke et al. |
| 5,549,115 A | 8/1996 | Morgan et al. |
| 5,549,659 A | 8/1996 | Johansen et al. |
| 5,565,759 A | 10/1996 | Dunstan et al. |
| 5,593,426 A | 1/1997 | Morgan et al. |
| 5,674,252 A | 10/1997 | Morgan et al. |
| 5,680,863 A | 10/1997 | Morgan et al. |
| 5,683,423 A | 11/1997 | Post et al. |
| 5,685,314 A | 11/1997 | Geheb et al. |
| 5,715,823 A | 2/1998 | Wood et al. |
| 5,716,380 A * | 2/1998 | Yerkovich ............ A61N 1/3925 607/2 |
| 5,724,985 A | 3/1998 | Snell et al. |
| 5,749,902 A | 5/1998 | Olson et al. |
| 5,749,913 A | 5/1998 | Cole et al. |
| 5,782,878 A | 7/1998 | Morgan et al. |
| 5,787,155 A | 7/1998 | Luna et al. |
| 5,814,089 A | 9/1998 | Stokes et al. |
| 5,836,993 A | 11/1998 | Cole et al. |
| 5,857,967 A | 1/1999 | Frid et al. |
| 5,879,374 A | 3/1999 | Powers et al. |
| 5,891,046 A | 4/1999 | Cyrus et al. |
| 5,891,049 A | 4/1999 | Cyrus et al. |
| 5,899,866 A | 5/1999 | Cyrus et al. |
| 5,921,938 A | 7/1999 | Aoyama et al. |
| 5,929,601 A | 7/1999 | Kaib et al. |
| 5,950,632 A | 9/1999 | Reber et al. |
| 5,951,485 A | 9/1999 | Cyrus et al. |
| D414,869 S | 10/1999 | Daynes et al. |
| 5,999,493 A | 12/1999 | Olson et al. |
| 6,024,699 A | 2/2000 | Surwit et al. |
| 6,041,257 A | 3/2000 | MacDuff et al. |
| 6,047,207 A | 4/2000 | MacDuff et al. |
| 6,057,758 A | 5/2000 | Dempsey et al. |
| 6,102,856 A | 8/2000 | Groff et al. |
| 6,111,505 A | 8/2000 | Wagener et al. |
| 6,134,468 A | 10/2000 | Morgan et al. |
| 6,141,584 A | 10/2000 | Rockwell et al. |
| 6,144,922 A | 11/2000 | Douglas et al. |
| 6,150,951 A | 11/2000 | Olejniczak et al. |
| 6,157,313 A | 12/2000 | Emmermann et al. |
| 6,183,417 B1 | 2/2001 | Geheb et al. |
| 6,188,407 B1 | 2/2001 | Smith et al. |
| 6,201,992 B1 | 3/2001 | Freeman et al. |
| 6,223,077 B1 | 4/2001 | Schweizer et al. |
| 6,275,737 B1 | 8/2001 | Mann et al. |
| 6,301,501 B1 | 10/2001 | Cronin et al. |
| 6,301,502 B1 | 10/2001 | Owen et al. |
| 6,304,780 B1 | 10/2001 | Owen et al. |
| 6,321,113 B1 | 11/2001 | Parker et al. |
| 6,323,782 B1 | 11/2001 | Stephens et al. |
| 6,334,070 B1 | 12/2001 | Nova et al. |
| 6,336,900 B1 | 1/2002 | Alleckson et al. |
| D455,492 S | 4/2002 | Daynes et al. |
| 6,370,428 B1 | 4/2002 | Snyder et al. |
| 6,374,138 B1 | 4/2002 | Owen et al. |
| 6,377,223 B1 * | 4/2002 | Clapp ................ A61B 5/0002 343/702 |
| 6,381,492 B1 | 4/2002 | Rockwell et al. |
| 6,402,691 B1 | 6/2002 | Peddicord et al. |
| 6,405,083 B1 | 6/2002 | Rockwell et al. |
| 6,422,669 B1 * | 7/2002 | Salvatori .............. A61N 1/3968 206/320 |
| 6,427,083 B1 | 7/2002 | Owen et al. |
| 6,434,429 B1 | 8/2002 | Kraus et al. |
| 6,438,417 B1 | 8/2002 | Rockwell et al. |
| 6,441,747 B1 | 8/2002 | Khair et al. |
| 6,493,581 B2 | 12/2002 | Russell et al. |
| 6,524,241 B2 | 2/2003 | Iliff et al. |
| 6,571,128 B2 | 5/2003 | Lebel et al. |
| 6,591,135 B2 * | 7/2003 | Palmer .................... A61B 5/04 607/34 |
| 6,594,634 B1 | 7/2003 | Hampton et al. |
| 6,597,948 B1 | 7/2003 | Rockwell et al. |
| 6,668,192 B1 | 12/2003 | Parker et al. |
| 6,771,172 B1 | 8/2004 | Robinson et al. |
| 6,957,102 B2 | 10/2005 | Silver et al. |
| 6,978,181 B1 | 12/2005 | Snell et al. |
| 7,006,865 B1 | 2/2006 | Cohen et al. |
| 7,110,825 B2 | 9/2006 | Vaynberg et al. |
| 7,570,994 B2 | 8/2009 | Tamura et al. |
| 8,040,246 B2 | 10/2011 | Graves et al. |
| D649,644 S | 11/2011 | Chai et al. |
| 8,054,177 B2 | 11/2011 | Graves et al. |
| D658,296 S | 4/2012 | Matheson et al. |
| 8,154,246 B1 | 4/2012 | Heitmann et al. |
| D693,006 S | 11/2013 | Arimitsu et al. |
| 8,594,784 B2 | 11/2013 | Schwibner et al. |
| 9,155,902 B2 | 10/2015 | Schwibner et al. |
| 9,168,386 B2 | 10/2015 | Schwibner et al. |
| 9,289,621 B2 | 3/2016 | Aoyama et al. |
| 2001/0041920 A1 | 11/2001 | Starkweather et al. |
| 2002/0103508 A1 | 8/2002 | Mathur et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0123673 A1 | 9/2002 | Webb et al. |
| 2002/0128689 A1 | 9/2002 | Connelly et al. |
| 2002/0128691 A1 | 9/2002 | Connelly et al. |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly et al. |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138103 A1 * | 9/2002 | Mulhauser et al. .............. 607/5 |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147470 A1 | 10/2002 | Weiner et al. |
| 2002/0177793 A1 * | 11/2002 | Sherman et al. .............. 601/41 |
| 2002/0183796 A1 | 12/2002 | Connelly et al. |
| 2002/0198569 A1 | 12/2002 | Foster et al. |
| 2003/0025602 A1 | 2/2003 | Medema et al. |
| 2003/0028219 A1 | 2/2003 | Powers et al. |
| 2003/0045905 A1 | 3/2003 | Daynes et al. |
| 2003/0050538 A1 | 3/2003 | Naghavi et al. |
| 2003/0058097 A1 | 3/2003 | Saltzstein et al. |
| 2003/0088275 A1 | 5/2003 | Palmer et al. |
| 2003/0097160 A1 | 5/2003 | Caby et al. |
| 2003/0109904 A1 | 6/2003 | Silver et al. |
| 2003/0167074 A1 | 9/2003 | Merry et al. |
| 2003/0212311 A1 | 11/2003 | Nova et al. |
| 2004/0049233 A1 | 3/2004 | Edwards et al. |
| 2004/0096808 A1 * | 5/2004 | Price et al. .................... 434/112 |
| 2004/0102167 A1 | 5/2004 | Shim et al. |
| 2004/0111122 A1 | 6/2004 | Daynes et al. |
| 2004/0122476 A1 * | 6/2004 | Wung ................ 607/5 |
| 2004/0162586 A1 * | 8/2004 | Covey et al. ...................... 607/5 |
| 2004/0204743 A1 | 10/2004 | McGrath et al. |
| 2005/0075671 A1 * | 4/2005 | Vaisnys et al. ................... 607/5 |
| 2005/0124866 A1 | 6/2005 | Elaz et al. |

(56) References Cited

U.S. PATENT DOCUMENTS

| | | | |
|---|---|---|---|
| 2005/0288571 | A1 | 12/2005 | Perkins et al. |
| 2006/0069326 | A1* | 3/2006 | Heath ............... A61H 31/005 601/41 |
| 2006/0142808 | A1* | 6/2006 | Pearce ................ A61N 1/39 607/5 |
| 2006/0149321 | A1 | 7/2006 | Merry et al. |
| 2006/0149323 | A1 | 7/2006 | Merry et al. |
| 2006/0173498 | A1 | 8/2006 | Banville et al. |
| 2007/0213775 | A1 | 9/2007 | Snyder et al. |
| 2008/0077185 | A1 | 3/2008 | Pearce et al. |
| 2008/0183229 | A1 | 7/2008 | Neumiller et al. |
| 2008/0221397 | A1 | 9/2008 | McMahon et al. |
| 2008/0221930 | A1* | 9/2008 | Wekell ............. A61B 5/02055 705/3 |
| 2008/0287859 | A1* | 11/2008 | Miller ............. A61B 17/3472 604/21 |

FOREIGN PATENT DOCUMENTS

| | | |
|---|---|---|
| EP | 1228782 | 8/2002 |
| EP | 1250944 | 10/2002 |
| WO | WO0070889 | 11/2000 |
| WO | WO01/66182 | 9/2001 |
| WO | WO02/060529 | 8/2002 |
| WO | WO 2004093979 | 4/2004 |
| WO | WO2005058413 | 6/2005 |
| WO | WO2005058416 | 6/2005 |
| WO | WO13056194 | 4/2013 |
| WO | WO03/009895 | 6/2013 |

OTHER PUBLICATIONS

Amendment, dated Jul. 11, 2013, U.S. Appl. No. 10/583,176, filed Mar. 5, 2008.
Non-Final Rejection, dated Jan. 16, 2013, U.S. Appl. No. 10/583,176, filed Mar. 5, 2008.
Amendment, dated Oct. 1, 2012, U.S. Appl. No. 10/583,176, filed Mar. 5, 2008.
Non-Final Rejection, dated May 1, 2012, U.S. Appl. No. 10/583,176, filed Mar. 5, 2008.
Amendment, dated Apr. 5, 2012, U.S. Appl. No. 10/583,176, filed Mar. 5, 2008.
Final Rejection, dated Nov. 17, 2011, U.S. Appl. No. 10/583,176, filed Mar. 5, 2008.
Amendment, dated Aug. 22, 2011, U.S. Appl. No. 10/583,176, filed Mar. 5, 2008.
Non-Final Rejection, dated May 20, 2011, U.S. Appl. No. 10/583,176, filed Mar. 5, 2008.
Notice of Allowance, dated Jan. 26, 2011, U.S. Appl. No. 10/583,209, filed Oct. 18, 2007.
Amendment, dated Jan. 26, 2011, U.S. Appl. No. 10/583,209, filed Oct. 18, 2007.
Amendment, dated Dec. 20, 2010, U.S. Appl. No. 10/583,209, filed Oct. 18, 2007.
Final Rejection, dated Oct. 19, 2010, U.S. Appl. No. 10/583,209, filed Oct. 18, 2007.
Amendment, dated Jun. 16, 2010, U.S. Appl. No. 10/583,209, filed Oct. 18, 2007.
Non-Final Rejection, dated Mar. 16, 2010, U.S. Appl. No. 10/583,209, filed Oct. 18, 2007.
Non-Final Rejection, dated Feb. 3, 2011, U.S. Appl. No. 11/256,275, filed Oct. 21, 2005.
Amendment, dated Apr. 20, 2010, U.S. Appl. No. 11/256,275, filed Oct. 21, 2005.
Final Rejection, dated Feb. 3, 2010, U.S. Appl. No. 11/256,275, filed Oct. 21, 2005.
Amendment, dated Sep. 9, 2009, U.S. Appl. No. 11/256,275, filed Oct. 21, 2005.
Non-Final Rejection, dated Jun. 9, 2009, U.S. Appl. No. 11/256,275, filed Oct. 21, 2005.
Amendment, dated Apr. 3, 2009, U.S. Appl. No. 11/256,275, filed Oct. 21, 2005.
Final Rejection, dated Jan. 6, 2009, U.S. Appl. No. 11/256,275, filed Oct. 21, 2005.
Amendment, dated Oct. 8, 2008, U.S. Appl. No. 11/256,275, filed Oct. 21, 2005.
Non-Final Rejection, dated Jun. 9, 2008, U.S. Appl. No. 11/256,275, filed Oct. 21, 2005.
Response to Restriction, dated May 14, 2008, U.S. Appl. No. 11/256,275, filed Oct. 21, 2005.
Restriction Requirement, dated Feb. 5, 2008, U.S. Appl. No. 11/256,275, filed Oct. 21, 2005.
Notice of Allowance, dated May 11, 2016, U.S. Appl. No. 14/498,735, filed Sep. 26, 2014.
Amendment, dated Dec. 31, 2015, U.S. Appl. No. 14/498,735, filed Sep. 26, 2014.
Non-Final Rejection, dated Sep. 15, 2015, U.S. Appl. No. 14/498,735, filed Sep. 26, 2014.
Preliminary Amendment, dated Sep. 26, 2014, U.S. Appl. No. 14/498,735, filed Sep. 26, 2014.
Notice of Allowance, dated Mar. 14, 2014, U.S. Appl. No. 10/583,175, filed Nov. 1, 2007.
Amendment, dated Feb. 11, 2014, U.S. Appl. No. 10/583,175, filed Nov. 1, 2007.
Non-Final Rejection, dated Nov. 22, 2013, U.S. Appl. No. 10/583,175, filed Nov. 1, 2007.
Advisory Action, dated Oct. 10, 2013, U.S. Appl. No. 10/583,175, filed Nov. 1, 2007.
Amendment, dated Sep. 27, 2013, U.S. Appl. No. 10/583,175, filed Nov. 1, 2007.
Final Rejection, dated Jul. 29, 2013, U.S. Appl. No. 10/583,175, filed Nov. 1, 2007.
Amendment, dated Jun. 14, 2013, U.S. Appl. No. 10/583,175, filed Nov. 1, 2007.
Non-Final Rejection, dated Feb. 28, 2013, U.S. Appl. No. 10/583,175, filed Nov. 1, 2007.
Amendment, dated Jul. 29, 2010, U.S. Appl. No. 10/583,175, filed Nov. 1, 2007.
Final Rejection, dated Apr. 29, 2010, U.S. Appl. No. 10/583,175, filed Nov. 1, 2007.
Amendment, dated Jan. 4, 2010, U.S. Appl. No. 10/583,175, filed Nov. 1, 2007.
Non-Final Rejection, dated Oct. 2, 2009, U.S. Appl. No. 10/583,175, filed Nov. 1, 2007.
Notice of Allowance, dated Jun. 26, 2014, U.S. Appl. No. 13/965,667, filed Aug. 13, 2013.
Amendment, dated May 9, 2013, U.S. Appl. No. 13/103,783, filed May 9, 2011.
Response, dated May 28, 2014, U.S. Appl. No. 13/965,667, filed Aug. 13, 2013.
Final Rejection, dated Feb. 28, 2014, U.S. Appl. No. 13/965,667, filed Aug. 13, 2013.
Amendment, dated Feb. 5, 2014, U.S. Appl. No. 13/965,667, filed Aug. 13, 2013.
Non-Final Rejection, dated Nov. 5, 2013, U.S. Appl. No. 13/965,667, filed Aug. 13, 2013.
Notice of Allowance, dated May 9, 2013, U.S. Appl. No. 13/103,783, filed May 9, 2011.
Response, dated May 2, 2013, U.S. Appl. No. 13/103,783, filed May 9, 2011.
Final Rejection, dated Feb. 1, 2013, U.S. Appl. No. 13/103,783, filed May 9, 2011.
Amendment, dated Feb. 28, 2012, U.S. Appl. No. 13/103,783, filed May 9, 2011.
Non-Final Rejection, dated Nov. 28, 2011, U.S. Appl. No. 13/103,783, filed May 9, 2011.
Preliminary Amendment, dated Jun. 8, 2011, U.S. Appl. No. 13/103,783, filed May 9, 2011.
Non-Final Rejection, dated Nov. 1, 2016, U.S. Appl. No. 14/310,841, filed Jun. 20, 2014.
Amendment, dated Sep. 27, 2016, U.S. Appl. No. 14/310,841, filed Jun. 20, 2014.

(56) References Cited

OTHER PUBLICATIONS

Final Rejection, dated Jul. 7, 2016, U.S. Appl. No. 14/310,841, filed Jun. 20, 2014.
Amendment, dated May 25, 2016, U.S. Appl. No. 14/310,841, filed Jun. 20, 2014.
Non-Final Rejection, dated Feb. 8, 2016, U.S. Appl. No. 14/310,841, filed Jun. 20, 2014.
Response, dated Jan. 11, 2016, U.S. Appl. No. 14/310,841, filed Jun. 20, 2014.
Requirement for Restriction/Election dated Nov. 9, 2015, U.S. Appl. No. 14/310,841, filed Jun. 20, 2014.
International Search Report and Written Opinion from International Application No. PCT/US2004/042376, dated Mar. 24, 2005.
International Preliminary Report on Patentability from International Application No. PCT/US2004/042376, dated Jun. 20, 2006.
International Search Report and Written Opinion from International Application No. PCT/US2004/042792, dated Jul. 20, 2005.
International Preliminary Report on Patentability from International Application No. PCT/US2004/042792, dated Jun. 20, 2006.
International Search Report and Written Opinion from International Application No. PCT/US2004/012421, dated Sep. 13, 2004.
International Preliminary Report on Patentability from International Application No. PCT/US2004/012421, dated Oct. 28, 2005.
International Search Report and Written Opinion from International Application No. PCT/US2004/042377, dated Jun. 20, 2006.
International Preliminary Examination Report, dated Nov. 12, 2004, International Application No. PCT/US03/28463, International Filing Date Sep. 11, 2003.
Non-Final Rejection dated Jun. 14, 2017, U.S. Appl. No. 12/139,359, filed Jun. 13, 2008.
Amendment dated Apr. 19, 2017, U.S. Appl. No. 12/139,359, filed Jun. 13, 2008.
Advisory Action dated Mar. 31, 2017, U.S. Appl. No. 12/139,359, filed Jun. 13, 2008.
Amendment After Final dated Mar. 31, 2017, U.S. Appl. No. 12/139,359, filed Jun. 13, 2008.
Response After Final Action dated Mar. 23, 2017, U.S. Appl. No. 12/139,359, filed Jun. 13, 2008.
Final Rejection dated Nov. 23, 2016, U.S. Appl. No. 12/139,359, filed Jun. 13, 2008.
Amendment dated Sep. 14, 2016, U.S. Appl. No. 12/139,359, filed Jun. 13, 2008.
Non-Final Rejection dated Jun. 15, 2016, U.S. Appl. No. 12/139,359, filed Jun. 13, 2008.
Amendment dated Mar. 15, 2016, U.S. Appl. No. 12/139,359, filed Jun. 13, 2008.
Final Rejection dated Dec. 15, 2015, U.S. Appl. No. 12/139,359, filed Jun. 13, 2008.
Amendment dated Sep. 29, 2015, U.S. Appl. No. 12/139,359, filed Jun. 13, 2008.
Non-Final Rejection dated Jun. 29, 2015, U.S. Appl. No. 12/139,359, filed Jun. 13, 2008.
Amendment dated May 26, 2015, U.S. Appl. No. 12/139,359, filed Jun. 13, 2008.
Final Rejection dated Mar. 22, 2011, U.S. Appl. No. 12/139,359, filed Jun. 13, 2008.
Amendment dated Jan. 5, 2011, U.S. Appl. No. 12/139,359, filed Jun. 13, 2008.
Non-Final Rejection dated Oct. 5, 2010, U.S. Appl. No. 12/139,359, filed Jun. 13, 2008.
Final Rejection dated Aug. 2, 2006, U.S. Appl. No. 10/378,001, filed Feb. 28, 2003.
Amendment dated May 30, 2006, U.S. Appl. No. 10/378,001, filed Feb. 28, 2003.
Non-Final Rejection dated Dec. 27, 2005, U.S. Appl. No. 10/378,001, filed Feb. 28, 2003.
Response to Rejection dated Nov. 21, 2005, U.S. Appl. No. 10/378,001, filed Feb. 28, 2003.
Requirement for Restriction dated Oct. 21, 2005, U.S. Appl. No. 10/378,001, filed Feb. 28, 2003.
Communication from the Examining Division dated Aug. 18, 2008, Application No. EP1617896.
Reply to Communication from the Examining Division dated Dec. 16, 2008, Application No. EP1617896.
Decision to Grant dated Aug. 6, 2009, Application No. EP1617896.
Communication from the Examining Division dated Jun. 29, 2017, Application No. EP12816583.4.
International Preliminary Report on Patentability dated Apr. 18, 2016, International Application No. PCT/US15/055095, international filing date Oct. 12, 2015.
International Preliminary Report on Patentability dated Nov. 11, 2014, PCT/US2012/071436, dated Apr. 10, 2013.
International Preliminary Report on Patentability dated Nov. 11, 2014, PCT/US2012/071461, dated Apr. 10, 2013, 14 pages.
International Preliminary Report on Patentability dated Nov. 11, 2014, PCT/US2012/071448, dated Feb. 8, 2013, 11 pages.
International Preliminary Report on Patentability dated Nov. 11, 2014, PCT/US2012/071450, dated May 24, 2013.
Advisory Action, dated May 12, 2015, U.S. Appl. No. 13/690,094, filed Nov. 30, 2012.
Amendment, dated Feb. 18, 2016, U.S. Appl. No. 13/690,094, filed Nov. 30, 2012.
Amendment, dated May 12, 2015, U.S. Appl. No. 13/690,094, filed Nov. 30, 2012.
Amendment, dated Jun. 2, 2015, U.S. Appl. No. 13/690,094, filed Nov. 30, 2012.
Preliminary Amendment, dated Aug. 14, 2013, U.S. Appl. No. 13/690,094, filed Nov. 30, 2012.
Response, dated Apr. 29, 2015, U.S. Appl. No. 13/690,094, filed Nov. 30, 2012.
Amendment, dated Feb. 5, 2016, U.S. Appl. No. 13/690,094, filed Nov. 30, 2012.
Amendment, dated Oct. 14, 2015, U.S. Appl. No. 13/690,094, filed Nov. 30, 2012.
Amendment, dated Jan. 19, 2015, U.S. Appl. No. 13/690,094, filed Nov. 30, 2012.
Amendment, dated Dec. 18, 2013, U.S. Appl. No. 13/690,094, filed Nov. 30, 2012.
Final Office Action dated Jan. 14, 2016, U.S. Appl. No. 13/690,056, filed Nov. 30, 2012.
Office Action dated Aug. 10, 2015, U.S. Appl. No. 13/690,056, filed Nov. 30, 2012.
Office Action dated Mar. 7, 2016, U.S. Appl. No. 13/690,056, filed Nov. 30, 2012.
Office Action dated Sep. 1, 2016, U.S. Appl. No. 13/690,056, filed Nov. 30, 2012.
Office Action dated Nov. 15, 2016, U.S. Appl. No. 13/690,056, filed Nov. 30, 2012.
Office Action dated Mar. 7, 2017, U.S. Appl. No. 13/690,056, filed Nov. 30, 2012.
Notice of Allowance dated Jun. 14, 2017, U.S. Appl. No. 13/690,056, filed Nov. 30, 2012.
Amendment, dated Oct. 28, 2016, U.S. Appl. No. 13/690,056, filed Nov. 30, 2012.
Amendment, dated Jun. 6, 2016, U.S. Appl. No. 13/690,056, filed Nov. 30, 2012.
Amendment, dated Oct. 5, 2015, U.S. Appl. No. 13/690,056, filed Nov. 30, 2012.
Preliminary Amendment, dated Aug. 14, 2013, U.S. Appl. No. 13/690,056, filed Nov. 30, 2012.
Amendment, dated Mar. 15, 2017, U.S. Appl. No. 13/690,056, filed Nov. 30, 2012.
Amendment, dated Nov. 28, 2016, U.S. Appl. No. 13/690,056, filed Nov. 30, 2012.
Final Office Action dated May 12, 2017, U.S. Appl. No. 15/152,248, filed May 11, 2016.
Office Action dated Nov. 23, 2016, U.S. Appl. No. 15/152,248, filed May 11, 2016.
Preliminary Amendment, dated Jan. 9, 2017, U.S. Appl. No. 15/152,248, filed May 11, 2016.
Preliminary Amendment, dated Oct. 28, 2016, U.S. Appl. No. 15/152,248, filed May 11, 2016.

(56) References Cited

OTHER PUBLICATIONS

Amendment, dated Mar. 23, 2017, U.S. Appl. No. 15/152,248, filed May 11, 2016.
Office Action dated Aug. 18, 2014, U.S. Appl. No. 29/452640, filed Apr. 19, 2013.
Notice of Allowance, dated Nov. 19, 2014, U.S. Appl. No. 29/452,640, filed Apr. 19, 2013.
Non-Final Rejection, dated Aug. 18, 2014, U.S. Appl. No. 29/452,640, filed Apr. 19, 2013.
Amendment, dated Nov. 3, 2014, U.S. Appl. No. 29/452,640, filed Apr. 19, 2013.
Amendment, dated Oct. 1, 2014, U.S. Appl. No. 29/452,640, filed Apr. 19, 2013.
Office Action dated Aug. 18, 2014, U.S. Appl. No. 29/440,594, filed Dec. 21, 2012.
Notice of Allowance, dated Nov. 28, 2014, U.S. Appl. No. 29/440,594, filed Dec. 21, 2012.
Response, dated Aug. 7, 2014, U.S. Appl. No. 29/440,594, filed Dec. 21, 2012.
Amendment, dated Nov. 3, 2014, U.S. Appl. No. 29/440,594, filed Dec. 21, 2012.
Amendment, dated Oct. 1, 2014, U.S. Appl. No. 29/440,594, filed Dec. 21, 2012.
Final Office Action dated Jan. 8, 2016, U.S. Appl. No. 13/690,031, filed Nov. 30, 2012.
Office Action dated Jul. 15, 2015, U.S. Appl. No. 13/690,031, filed Nov. 30, 2012.
Notice of Allowance, dated Jun. 7, 2016, U.S. Appl. No. 13/690,031, filed Nov. 30, 2012.
Notice of Allowance, dated Mar. 21, 2016, U.S. Appl. No. 13/690,031, filed Nov. 30, 2012.
Amendment, dated Aug. 25, 2016, U.S. Appl. No. 13/690,031, filed Nov. 30, 2012.
Amendment, dated May 11, 2016, U.S. Appl. No. 13/690,031, filed Nov. 30, 2012.
Preliminary Amendment, dated Aug. 14, 2013, U.S. Appl. No. 13/690,031, filed Nov. 30, 2012.
Preliminary Amendment, dated Apr. 29, 2013, U.S. Appl. No. 13/690,031, filed Nov. 30, 2012.
Amendment, dated Aug. 23, 2016, U.S. Appl. No. 13/690,031, filed Nov. 30, 2012.
Amendment, dated Oct. 5, 2015, U.S. Appl. No. 13/690,031, filed Nov. 30, 2012.
Preliminary Amendment, dated Jan. 9, 2017, U.S. Appl. No. 15/283,966, filed Oct. 3, 2016.
Preliminary Amendment, dated Oct. 28, 2016, U.S. Appl. No. 15/283,966, filed Oct. 3, 2016.
U.S. Appl. No. 60/464,860, filed Apr. 22, 2003, Christopher Pearce et al. 7 pages.
U.S. Appl. No. 60/530,151, filed Dec. 17, 2003, Christopher Pearce et al. 125 pages.
International Search Report & Written Opinion dated Apr. 21, 2016, International Application No. PCT/US15/055095, international filed Oct. 12, 2015.
International Search Report and Written Opinion, PCT/US2012/071436, dated Apr. 10, 2013, 13 pages.
International Search Report and Written Opinion, PCT/US2012/071461, dated Apr. 10, 2013, 14 pages.
International Search Report and Written Opinion, PCT/US2012/071448, dated Feb. 8, 2013, 11 pages.
International Search Report and Written Opinion, PCT/US2012/071450, dated May 24, 2013, 10 pages.
Non-Final Action, dated Mar. 13, 2017, U.S. Appl. No. 15/057,468, filed Mar. 1, 2016.
Non-Final Action, dated Apr. 14, 2016, U.S. Appl. No. 15/057,468, filed Mar. 1, 2016.
Notice of Allowance, dated Jan. 13, 2017, U.S. Appl. No. 15/057,468, filed Mar. 1, 2016.
Notice of Allowance, dated Nov. 21, 2016, U.S. Appl. No. 15/057,468, filed Mar. 1, 2016.
Notice of Allowance, dated Aug. 31, 2016, U.S. Appl. No. 15/057,468, filed Mar. 1, 2016.
Amendment, dated Jan. 13, 2017, U.S. Appl. No. 15/057,468, filed Mar. 1, 2016.
Amendment, dated Nov. 21, 2016, U.S. Appl. No. 15/057,468, filed Mar. 1, 2016.
Amendment, dated Jan. 6, 2017, U.S. Appl. No. 15/057,468, filed Mar. 1, 2016.
Amendment, dated Oct. 31, 2016, U.S. Appl. No. 15/057,468, filed Mar. 1, 2016.
Amendment, dated Jul. 8, 2016, U.S. Appl. No. 15/057,468, filed Mar. 1, 2016.
Claims of U.S. U.S. Appl. No. 15/057,468 as of Jul. 8, 2016.
Office Action dated Apr. 1, 2015, U.S. Appl. No. 13/836,769, filed Mar. 15, 2013.
Final Office Action dated Oct. 28, 2015, U.S. Appl. No. 13/836,769, filed Mar. 15, 2011.
Advisory Action dated Jan. 21, 2016, U.S. Appl. No. 13/836,769, filed Mar. 15, 2013.
Office Action dated Feb. 18, 2016, U.S. Appl. No. 13/836,769, filed Mar. 15, 2013.
Final Office Action dated Jun. 15, 2016, U.S. Appl. No. 13/836,769, filed Mar. 15, 2011.
Notice of Allowance, dated Dec. 30, 2016, U.S. Appl. No. 13/836,769, filed Mar. 15, 2011.
Notice of Allowance, dated Aug. 18, 2016, U.S. Appl. No. 13/836,769, filed Mar. 15, 2011.
Advisory Action, mailed Jan. 21, 2016, Application No. 13/836,769, filed Mar. 15, 2013.
Response After Final Action, dated Aug. 12, 2016, U.S. Appl. No. 13/836,769, filed Mar. 15, 2013.
Amendment dated Jun. 6, 2016. U.S. Appl. No. 13/836,769, filed Mar. 15, 2013.
Amendment dated Jul. 31, 2015, U.S. Appl. No. 13/836,769, filed Mar. 15, 2013.
Preliminary Amendment, dated Nov. 18, 2016, U.S. Appl. No. 13/836,769, filed Mar. 15, 2013.
Office Action dated Mar. 4, 2016, U.S. Appl. No. 13/690,075, filed Nov. 30, 2012.
Office Action dated Jul. 15, 2015, U.S. Appl. No. 13/690,075, filed Nov. 30, 2012.
Final Office Action dated Oct. 18, 2016 , U.S. Appl. No. 13/690,075, filed Nov. 30, 2012.
Final Office Action dated Jan. 13, 2016, U.S. Appl. No. 13/690,075, filed Nov. 30, 2012.
Notice of Allowance, dated Feb. 8, 2017, U.S. Appl. No. 13/690,075, filed Nov. 30, 2012.
Response to Restriction, dated Oct. 28, 2014, U.S. Appl. No. 13/690,075, filed Nov. 30, 2012.
Restriction Requirement, dated Oct. 20, 2014, U.S. Appl. No. 13/690,075, filed Nov. 30, 2012.
Amendment, dated Jan. 27, 2017, U.S. Appl. No. 13/690,075, filed Nov. 30, 2012.
Preliminary Amendment, dated Aug. 14, 2013, U.S. Appl. No. 13/690,075, filed Nov. 30, 2012.
Amendment, dated Jun. 15, 2016, U.S. Appl. No. 13/690,075, filed Nov. 30, 2012.
Amendment, dated Oct. 5, 2015, U.S. Appl. No. 13/690,075, filed Nov. 30, 2012.
Amendment After Notice of Allowance, dated Mar. 16, 2017, U.S. Appl. No. 13/690,075, filed Nov. 30, 2012.
Notice of Allowance, dated May 5, 2017, U.S. Appl. No. 13/690,075, filed Nov. 30, 2012.
Final Office Action dated Mar. 24, 2014, U.S. Appl. No. 13/690,094, filed Nov. 30, 2012.
Final Office Action dated Mar. 3, 2015, U.S. Appl. No. 13/690,094, filed Nov. 30, 2012.
Office Action dated Sep. 26, 2013, U.S. Appl. No. 13/690,094, filed Nov. 30, 2012.
Office Action dated Sep. 24, 2014, U.S. Appl. No. 13/690,094, filed Nov. 30, 2012.
Office Action dated Jul. 14, 2015, U.S. Appl. No. 13/690,094, filed Nov. 30, 2012.

(56) References Cited

OTHER PUBLICATIONS

Notice of Allowance, dated Feb. 18, 2016, U.S. Appl. No. 13/690,094, filed Nov. 30, 2012.
Notice of Allowance, dated Nov. 9, 2015, U.S. Appl. No. 13/690,094, filed Nov. 30, 2012.
Notice of Allowance dated Sep. 19, 2017, U.S. Appl. No. 15/057,468, filed Mar. 1, 2016.
Amendment filed Mar. 19, 2018, U.S. Appl. No. 13/836,769, filed Mar. 15, 2013.
Office Action dated Oct. 19, 2017, U.S. Appl. No. 13/836,769, filed Mar. 15, 2013.
Final Office Action dated Mar. 19, 2018, U.S. Appl. No. 13/690,075, filed Nov. 30, 2012.
Amendment dated Dec. 21, 2017, U.S. Appl. No. 13/690,075, filed Nov. 30, 2012.
Office Action dated Aug. 21, 2017, U.S. Appl. No. 13/690,075, filed Nov. 30, 2012.
Notice of Allowance dated Jan. 19, 2018, U.S. Appl. No. 13/690,056, filed Nov. 30, 2012.
Notice of Allowance dated Jan. 31, 2018, U.S. Appl. No. 15/152,248, filed May 11, 2016.
Response dated Oct. 12, 2017, U.S. Appl. No. 15/152,248, filed May 11, 2016.
Final Rejection dated Jan. 11, 2018, U.S. Appl. No. 12/139,359, filed Jun. 13, 2008.
Amendment dated Apr. 11, 2018, U.S. Appl. No. 12/139,359, filed Jun. 13, 2008.
Amendment dated Dec. 14, 2017, U.S. Appl. No. 12/139,359, filed Jun. 13, 2008.
Amendment filed Mar. 13, 2018, U.S. Appl. No. 15/245,450, filed Aug. 24, 2016.
Notice of Allowance dated Jul. 13, 2018, U.S. Appl. No. 13/690,075, filed Nov. 30, 2012.
Notice of Allowance dated Jul. 13, 2018, U.S. Appl. No. 15/152,248, filed May 11, 2016.
Notice of Allowance dated Jun. 21, 2018, U.S. Appl. No. 15/283,966, filed Oct. 3, 2016.
Notice of Allowance dated Aug. 15, 2018, U.S. Appl. No. 15/245,450, filed Aug. 24, 2016.
Response to Final Office Action dated Jul. 27, 2018, U.S. Appl. No. 15/245,450, filed Aug. 24, 2016.
Final Office Action dated Jul. 13, 2018, U.S. Appl. No. 15/245,450, filed Aug. 24, 2016.
Amendment filed Aug. 23, 2018, U.S. Appl. No. 13/836,769, filed Mar. 15, 2013.
Amendment, dated Jul. 13, 2017, U.S. Appl. No. 15/057,468, filed Mar. 1, 2016.
RCE_Amendment dated, dated Apr. 12, 2017, U.S. Appl. No. 13/690,075, filed Nov. 30, 2012.

* cited by examiner

DEFIBRILLATOR PATIENT MONITORING POD

CROSS REFERENCE

This application claims priority to International PCT Application No. PCT/US2004/012421 titled "Defibrillator/Monitor System Having a Pod with Leads Capable of Wirelessly Communicating" filed on Apr. 22, 2004, and to U.S. Provisional Application Ser. No. 60/530,151 titled "Defibrillator/Monitor System Having a Pod with Leads Capable of Wirelessly Communicating" filed on Dec. 17, 2003, which are both hereby incorporated by reference in their entirety.

This disclosure is related to the following co-pending PCT applications entitled "AN EXTERNAL DEFIBRILLATOR WITH POWER AND BATTERY SHARING CAPABILITIES WITH A POD" filed Dec. 17, 2004, and "DEFIBRILLATOR/MONITOR SYSTEM HAVING A POD WITH LEADS CAPABLE OF WIRELESSLY COMMUNICATING" filed Dec. 17, 2004, which are herein incorporated by reference in their entirety and not admitted as prior art with respect to the present disclosure by its mention in this section.

TECHNICAL FIELD

The teachings relates to medical devices, and in particular, to defibrillation/monitor systems having a detachable pod with leads.

BACKGROUND

Each day thousands of Americans are victims of cardiac emergencies. Cardiac emergencies typically strike without warning, oftentimes striking people with no history of heart disease. The most common cardiac emergency is sudden cardiac arrest ("SCA"). It is estimated more than 1000 people per day are victims of SCA in the United States alone.

SCA occurs when the heart stops pumping blood. Usually SCA is due to abnormal electrical activity in the heart, resulting in an abnormal rhythm (arrhythmia). One such abnormal rhythm, ventricular fibrillation (VF), is caused by abnormal and very fast electrical activity in the heart. During VF the heart cannot pump blood effectively. Because blood may no longer be pumping effectively during VF, the chances of surviving decreases with time after the onset of the emergency. Brain damage can occur after the brain is deprived of oxygen for four to six minutes.

Applying an electric shock to the patient's heart through the use of a defibrillator treats VF. The shock clears the heart of the abnormal electrical activity (in a process called "defibrillation") by depolarizing a critical mass of myocardial cells to allow spontaneous organized myocardial depolarization to resume.

Cardiac arrest is a life-threatening medical condition that may be treated with external defibrillation. External defibrillation includes applying electrodes to the patient's chest and delivering an electric shock to the patient to depolarize the patient's heart and restore normal sinus rhythm. The chance a patient's heart can be successfully defibrillated increases significantly if a defibrillation pulse is applied quickly.

In a scenario where a paramedic is responding to an emergency call with a non-specific patient condition, for example, there has been a car accident. The paramedic will typically carry his or her own defibrillator/monitor, a gurney, and drug box, and other supplies considered essential. If, perhaps, the car has driven off an embankment, the paramedic will have a long distance to run with all this equipment. This slows the response time to a call where someone may be bleeding to death. Smaller lighter equipment is always demanded by paramedics to save them time and effort, and allow them to get to the scene earlier. For just this reason, some paramedics will opt to carry only an AED (Automatic External Defibrillator) to the scene, and move the patient into the ambulance as quickly as possible, where other, more advanced monitoring equipment is available. In some countries, this approach has been incorporated into standard operating protocols, where the ambulance carries both ALS (advanced life support) equipment (which typically would include a multi-parameter monitor and defibrillator) and an AED. This approach, while effectively giving the user the choice of equipment to carry, forces the paramedic to learn two different defibrillators. The approach also forces the paramedics to possibly transfer the patient from one machine to the other once in the ambulance. It also adds costs to the ambulance service and potentially causes lost data between the two defibrillators for critical minutes, which may negatively impact the ability of EP Lab (Electro-Physiology Lab) doctors to determine the original cardiac condition.

Previous attempts to address the issue of product weight have done so by creating a manual defibrillator that separates from a patient monitor, or an AED, which separates from a single-channel patient monitor, or a manual defibrillator/pacemaker that separates from a 12-lead ECG monitor. These products suffer from limitations by the present standards, such as: limited capture of patient data, limited ability to monitor all necessary patient vital signs, and possible unreliability due to the nature of the electrical contacts between the two devices (e.g., dirt, mud, and damage to the case which could affect alignment of electrical contacts, thus preventing full functionality of the devices when mated).

In a scenario where a patient on a gurney is being transported through narrow doorways and down stairwells to an ambulance, or the situation where a patient is in an ambulance moving on a road at high speed with patient cables and TV (intravenous) lines running between the patient and other equipment within the ambulance. If the monitoring/therapeutic device is large or the route to the ambulance is particularly difficult, the paramedic might elect to carry the device separately from the gurney to prevent the device falling off the gurney or onto the patient. However, the paramedic is now restricted in his or her ability to detach the device from the gurney due to the number and length of patient cables between the device and the patient. Similar restrictions occur once the patient is loaded into a patient transport vehicle or when the patient is transferred from the ambulance to the emergency department. The number of cables and their similarity in color or dissimilarity in length can all contribute to delays in treating or transferring the patient and can restrict the paramedics mobility when treating the patient in a confined space. Additionally, delays may be created with cables having become tangled, or even cut, from their previous uses.

The prior art has tried to solve this problem by providing a wireless module that transmits data to a patient monitor, such as the MobiMed offered for Sale by Ortivus. However, this device does not include a defibrillator and does not have the capability to provide any therapeutic functions such as pacing, defibrillation or synchronous cardioversion without attaching another monitor/defibrillator to the patient, which further increases the complexity and ambulance provider cost. Additionally, the Ortivus patient module does not offer replaceable batteries so functionality is severely limited if a reliable source of battery charging is not available, or if the transport time is excessively long. Additionally, the Ortivus device does not offer a display to allow visual monitoring of the waveforms or vital signs if the other module is out of range or obscured.

SUMMARY

A patient parameter monitoring pod in embodiments of the teachings may include one or more of the following features: (a) portable housing containing a power supply, (b) a patient parameter module connectable to a patient via lead cables to collect patient data, the patient data including at least one vital sign, (c) a transceiver adapted to wirelessly transmit the patient data to a defibrillator, (d) a data port adapted to supply the patient data via a direct electrical connection to the defibrillator, and (e) a carrying handle extending from the housing proximate a patient lead cable port that permits connection of the lead cables to the pod, the carrying handle positioned to protect the patient lead cable port and the patient lead cables attached to the port from direct impact.

A patient parameter monitoring pod in embodiments of the teachings may include one or more of the following features: (a) a housing holding a power supply, (b) patient lead cables attachable between a patient and the housing to collect patient data, the patient data including at least one vital sign, (c) a carrying handle extending from the housing proximate the patient lead cable port, the carrying handle positioned to protect the patient lead cable port and the patient lead cables attached to the port from direct impact, (d) a communications module adapted to send the patient data to a defibrillator, (e) a lead cable comb separator, the separator holding the lead cables apart from each other, and (f) a carrying strap connected to one of the pod and the bag.

A patient parameter monitoring pod in embodiments of the teachings may include one or more of the following features: (a) a portable patient monitoring pod and a component storage bag, the pod having an outer housing, a patient parameter module, and a data port, the patient parameter module connectable to a patient via lead cables to collect patient data, the patient data including at least one vital sign, the data port being exposed on the housing and adapted to supply the patient data via a direct electrical connection to a defibrillator, the component storage bag having pockets for holding the pod and components of the pod, the storage bag having openings exposing the data port and permitting passage therethrough of the patient lead cables, (b) a carrying handle extending from the housing proximate a patient lead cable port that permits connection of the lead cables to the pod, the carrying handle positioned to protect the patient lead cable port and the patient lead cables attached to the port from direct impact, and (c) a lead cable comb separator, the separator holding the lead cables apart from each other.

DETAILED DESCRIPTION

Figure 1:
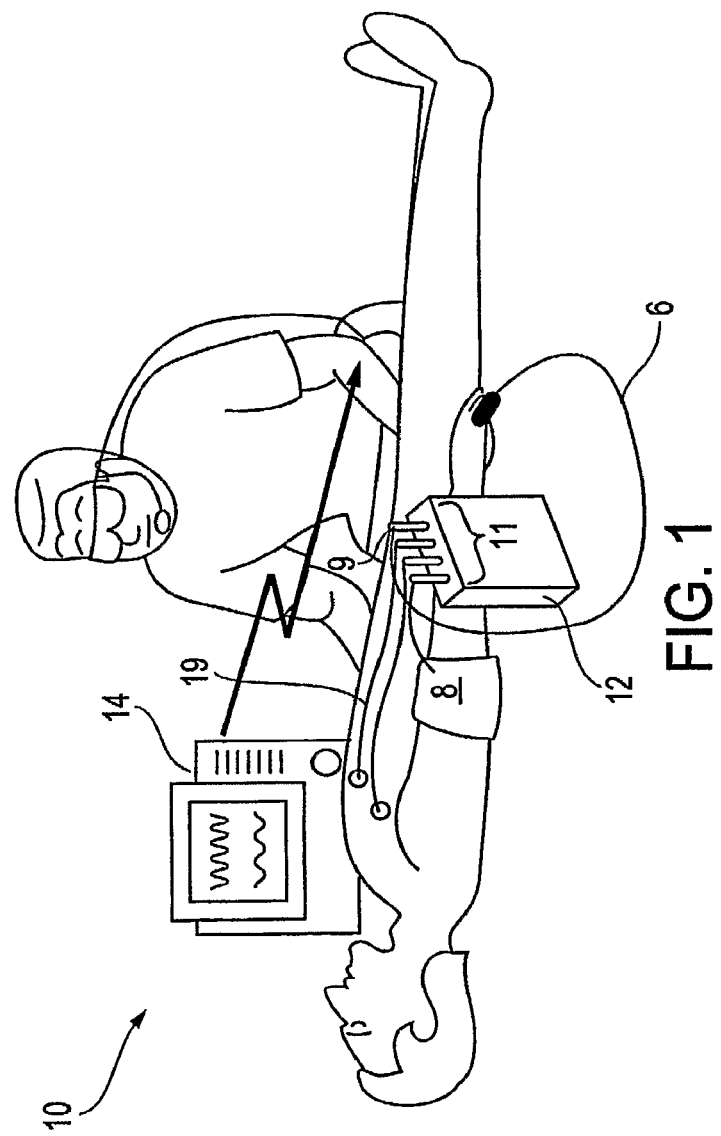
FIG. 1 is a pictorial representation of an external defibrillator having a patient module with a defibrillator/monitor in an embodiment of the present teachings [could we add in defib cables in FIG. 1 from the base to show that it has these, also add in a blurb in the description for FIG. 1]

The following discussion is presented to enable a person skilled in the art to make and use the present teachings. Various modifications to the illustrated embodiments will be readily apparent to those skilled in the art, and the generic principles herein may be applied to other embodiments and applications without departing from the present teachings. Thus, the present teachings are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the present teachings. Skilled artisans will recognize the examples provided herein have many useful alternatives and fall within the scope of the present teachings.

With reference to FIG. 1, a pictorial representation of an external defibrillator having a patient module with a defibrillator/monitor in an embodiment of the present teachings is shown. External defibrillator 10 is comprised of two components patient module (pod) 12 and defibrillator/monitor (base) 14, which communicate patient data (e.g., vital signs) and share common replaceable battery technology. Pod 12 generally rests within base 14, generally in the back of base 14. The operator, during an emergency, has the option of carrying base 14 with pod 12 attached or simply carrying pod 12 to the emergency site. Since pod 12 is smaller and lighter than base 14, generally it will be easier for the operator to simply carry pod 12. By carrying pod 12, the operator is free to carry more ALS equipment and not be slowed by the heavier and more awkward base 14.

Pod 12 connects to a patient via several leads in order to measure the patient's vital signs. Pod 12 communicates the patient's vital signs either wirelessly or via an electrical connection to defibrillator monitor 14. The patient data or vital signs collected may include 3, 4, and 5 lead ECG readings, 12 lead ECG readings, non-invasive blood pressure (NIBP), pulse oximeter data, capnography data, invasive blood pressure, body temperature, $CO_2$ levels, and additional patient monitoring functions. Additionally, pod 12 may include a small display 82 (FIG. 4) replicating some or all of the information such as waveforms, numerical data, and vital signs being transmitted to base 14. The patient data or vital signs may be collected with a multitude of leads 11 such as an ECG lead 19, a non-invasive blood pressure lead 8, and pulse oximeter lead 6, extending from patient lead cable port 9 that may include many inputs if multiple lead cables are used. Base 14 includes a therapy module 56 (FIG. 3) and therapy cables. Therapy module 56 has the capability to provide therapeutic functions such as pacing, defibrillation, or synchronous cardioversion without attaching another monitor/defibrillator to the patient. The therapy cables typically include patient paddles or electrodes that attach between the patient and base 14 in order to deliver the therapy to the patient. Since pod 12 connects to the patient and transmits vital signs to base 14, then base 14 need not also have patient monitoring cables. Accordingly, paramedic mobility and ease of use are greatly increased. Therapy module 56 in base 14 may be configurable in either an ALS mode or an AED mode. The ALS mode includes a multi-parameter monitoring capability and all of the defibrillator therapy delivery capability. Additionally base unit 14 may be just an AED.

Figure 2:
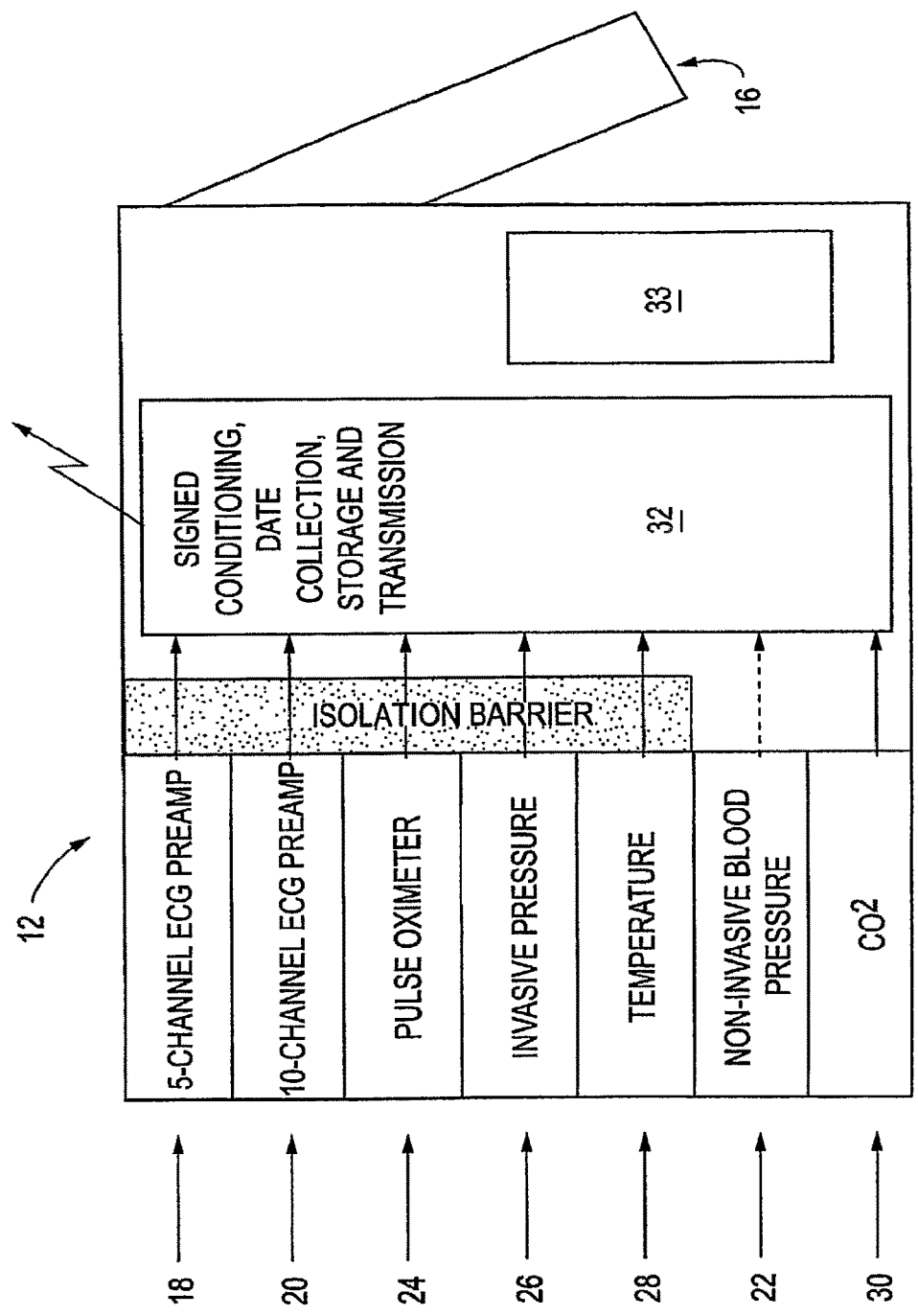
FIG. 2 is an upper level pictorial representation of a patient module in an embodiment of the present teachings.

With reference to FIG. 2, an upper level pictorial representation of a patient module in an embodiment of the present teachings is shown. Generally, pod 12 uses replaceable or rechargeable batteries 16 for power and comprises any combination of the following features: 3, 4, and 5 lead ECG inputs 18, 12 lead ECG inputs 20, non-invasive blood pressure (NIBP) input 22, pulse oximeter input 24, capnography input (not shown), invasive blood pressure input 26, temperature input 28, $CO_2$ input 30, additional patient monitoring functions, wireless (RF) transceiver 32 to transmit any or all real time patient data to base 14. Transceiver 32 can be a wireless BlueTooth module commercially available from TDK, however, transceiver 32 can be any transceiver such as WiFi (802.11), Wirelesse WAN (CDMA, GSM, GPRS, UTMS, etc.), or a wired Fire-Wire (IEEE 1394) without departing from the spirit of the present teachings. Additionally, pod 12 may include a small display 82 (FIG. 4) replicating some or all of the information such as waveforms, numerical data, and vital signs being transmitted to base 14. Additionally, pod 12 includes some means by which it can be attached to base 14 for the purpose of carrying base 14 to an emergency scene as is discussed in P.C.T. Application Serial No. US04/12421. Additionally, pod 12 may have a feature allowing it to be easily secured to a gurney or hospital bed.

Figure 3:
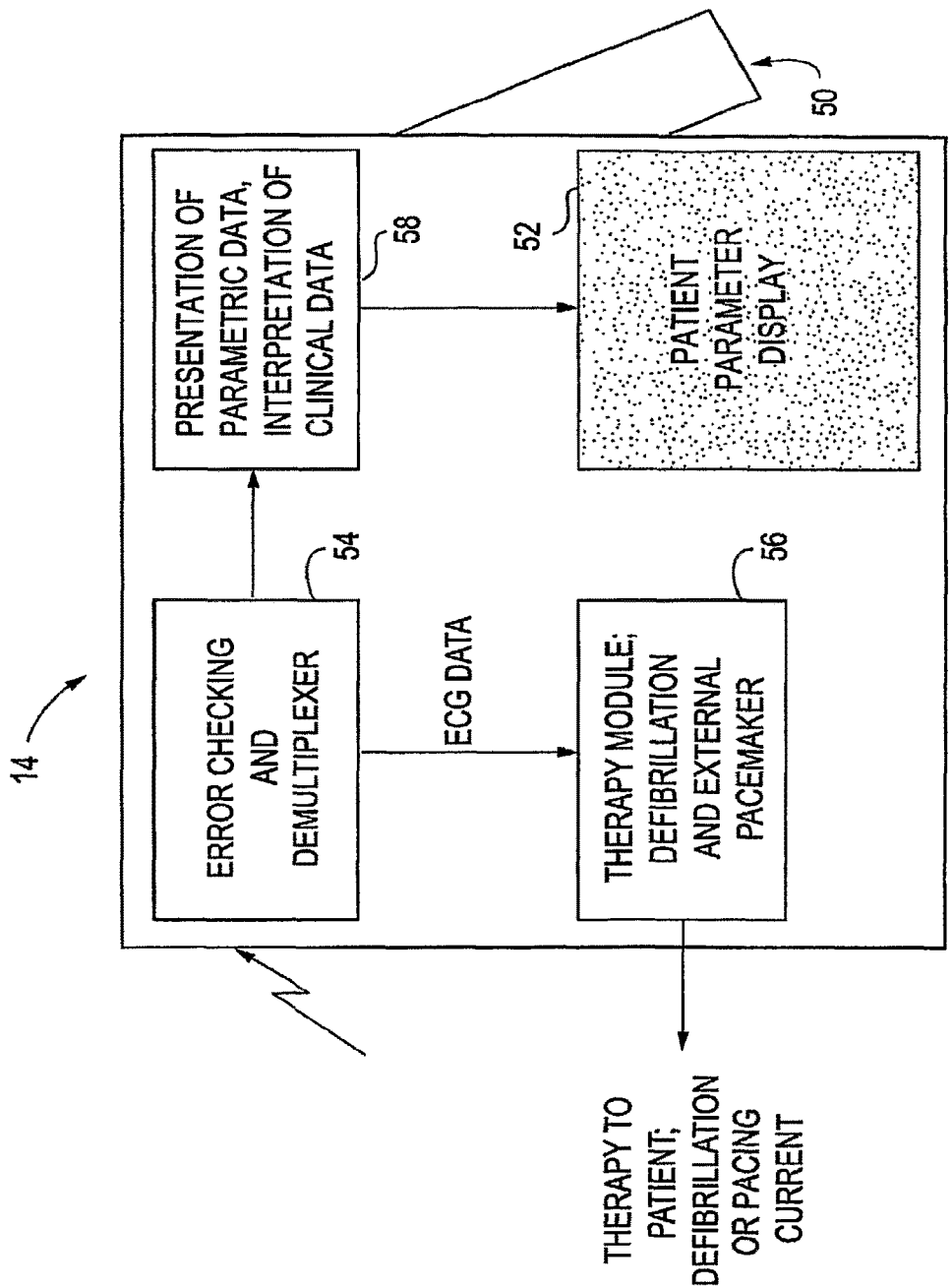
FIG. 3 is an upper level pictorial representation of a defibrillator/monitor in an embodiment of the present teachings.

With reference to FIG. 3, an upper level pictorial representation of a defibrillator/monitor in an embodiment of the present teachings is shown. Base 14 uses a replaceable or rechargeable battery 50 for power. Batteries 16 and 50 are generally similar in battery chemistry, electrical, and mechanical features to permit the interchangeability between batteries 16 and 50. Batteries 16 and 50 can be a LiIon battery providing 16 volts and 3.8 amps, however, most any type of battery can be used without departing from the spirit of the teachings. Additionally, base 14 comprises a display 52 sufficient to show current and historical patient data, a transceiver (similar to transceiver 32 [not shown]) to send acquired patient data onto a receiving station or third party data receiver, a module 56 to synchronize shocks and pacing pulses to the patient's intrinsic rhythm from data acquired by a pod 12, an error checking and de-multiplexing module 54 receiving and processing data received from pod 12, and a data interpretation module 58 which analyzes data acquired by pod 12 and makes certain interpretive statements on the patient's cardiac or respiratory condition, displays vital sign trends, and provides additional functions found in ALS monitoring products.

Figure 4:
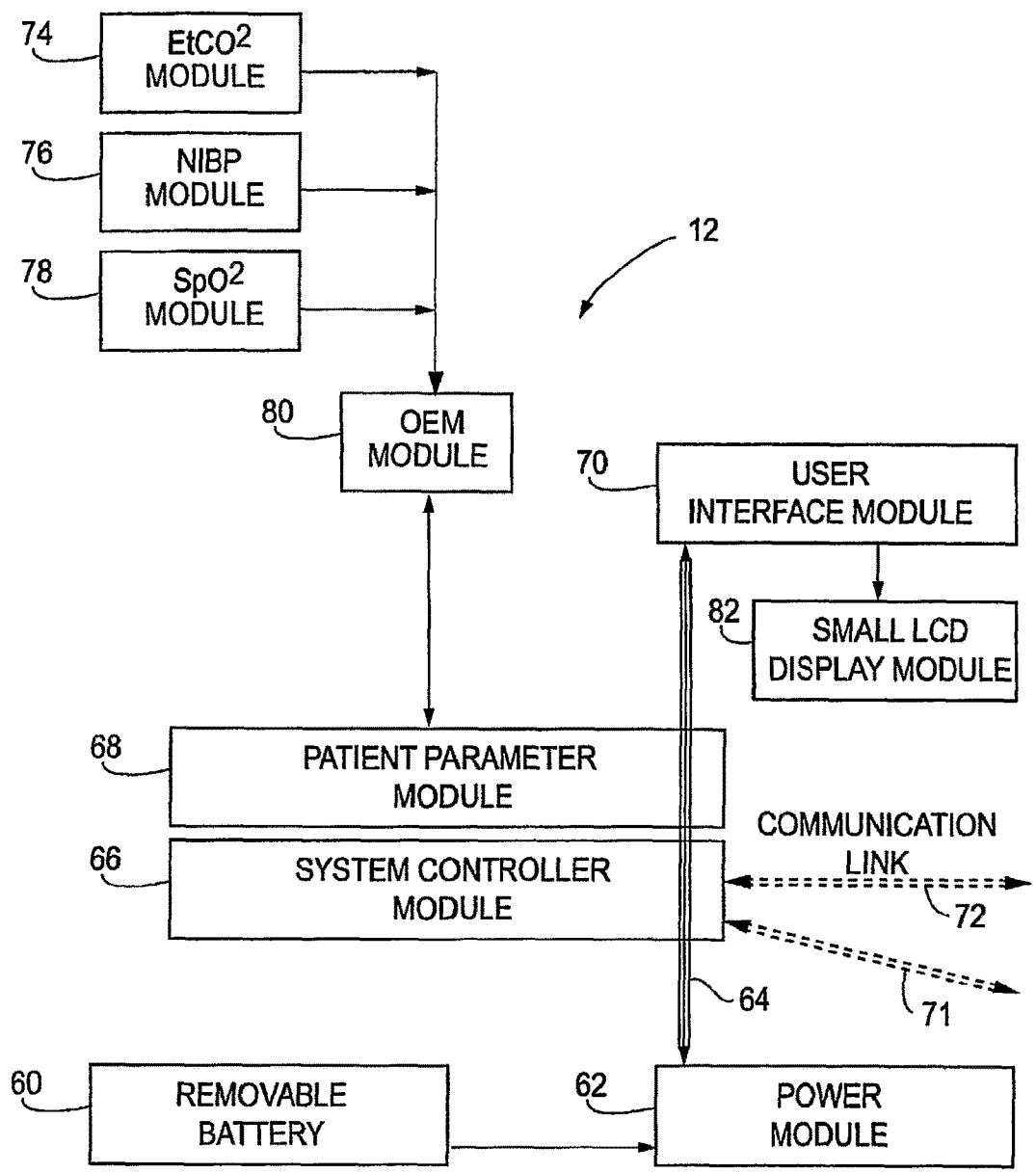
FIG. 4 is a schematic view of a patient module in an embodiment of the present teachings.

With reference to FIG. 4, a schematic view of a patient monitor in an embodiment of the present teachings is shown. As discussed above, pod 12 can be powered from a removable/rechargeable battery 60. Power module 62 processes the incoming power into appropriate power levels for each of the internal components. Power module 62 routes the pod's power supply through main power and data bus 64 to system controller module 66, patient parameter module 68, and operator interface module 70. As discussed above, pod 12 can be used wirelessly, however, it is helpful if pod 12 is directly connected through a tethered cable 46 (FIGS. 18 and 19) or through attachment to a connector to utilize the speed of data bus 64.

Figure 18:
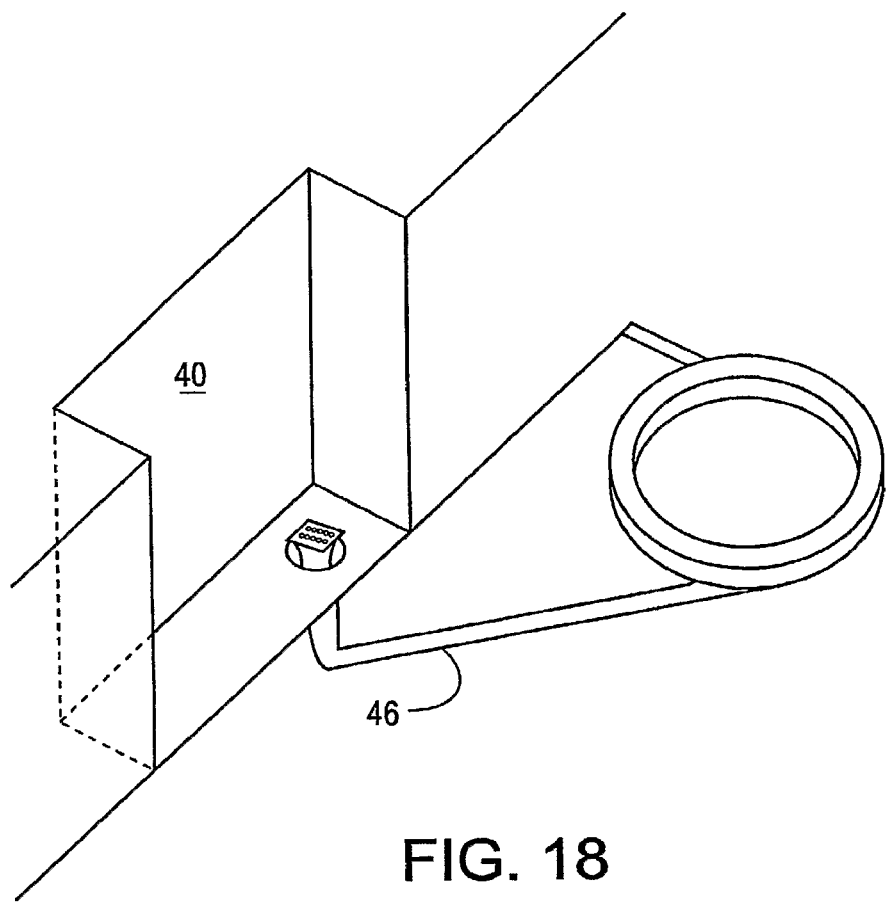
FIG. 18 is a pictorial representation of a mating assembly having a tethered connector in an embodiment of the present teachings.
Figure 19:
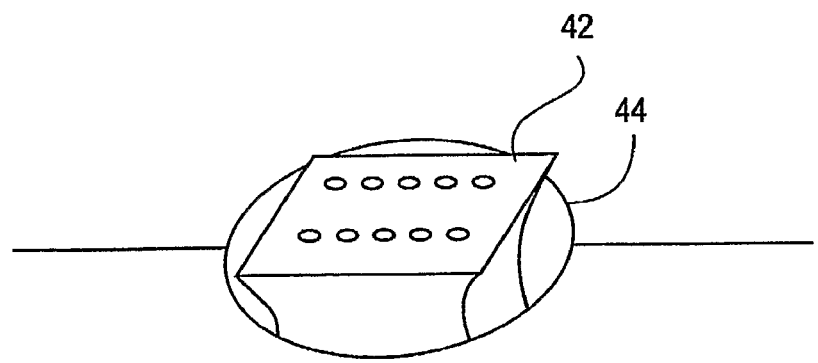
FIG. 19 is a pictorial representation of a mating assembly having a tethered connector in an embodiment of the present teachings.

With reference to FIGS. 18 and 19, a pictorial representation of a mating assembly having a tethered connector in an embodiment of the present teachings is shown. In this embodiment, a pod similar to 12 rests within slot 40 and connects to base-to-pod connector 42, which allows base 14 and a pod to communicate with each other. Base-to-pod connector 42 rests freely within connector cavity 44, which allows connector cable 46 to retractably exit and enter base 14. Tethered cable 46 allows a pod to mate with and rest within base 14 or mate with base 14 when not docked within slot 40. It is sometimes helpful that base 14 communicate with a pod through tethered cable 46 since communications through a direct connection is generally faster. This is the case in the present embodiment as base 14 is equipped with a USB bus, which provides quick communication of information between a pod and base 14. Base 14 is also able to automatically detect when tethered cable 46 is plugged in so direct communications can be established immediately. A direct communication between a pod and base 14 can be established. This automatic establishment of direct communication between a pod and base 14 includes when a pod is docked within base 14 and a connection is made between a pod and base 14 through connector 42.

Generally base 14 and a pod communicate wirelessly to assist in preventing the tangling of cables, which can occur between a patient and base 14, particularly when transporting patients. Tethered cable 46 provides a system for use when the wireless link between pod 12 and base 14 fails for whatever reason or when precise signal synchronization demands a wired connection. Tethered cable 46 also provides the added advantage in that the user cannot lose cable 46 because it is tethered to base 14. Wireless links can impose a delay in communication between a pod and base 14 longer than may be experienced with a cable. When communications between base 14 and a pod require a faster response time (such as application of synchronous cardioversion or pacing where information from a pod must be transmitted to base 14), the user is advised of the need to plug cable 46 into the pod. The user is provided a user interface message to inform them of the need to attach cable 46.

With reference again to FIG. 4, system controller module 66 controls interaction of all the pod's modules through data bus 64 and interaction with base 14 through a wired connection, such as tethered cable 46 or wireless (e.g., IrDA, RF, etc.) communication link 72 which would be transmitted by transceiver 32. System controller module 66 would also control interaction of separate pod's through communication link 71 which could be a direct connector 570 (FIG. 4A), or wireless transmitted by transceiver 32. Patient parameter module 68 monitors functions such as invasive blood pressure, patient's temperature, and inputs from the pod leads. Module 68 further collects inputs from EtCO2 module 74, NIBP module 76, and SpO2 module 78 through OEM module 80. Patient parameter module 68 takes all of these inputs and processes them for display and routes only a limited number of inputs to small LCD display module 82 through operator interface module 70. Operator Interface module 70 allows the operator to primarily interact with pod 12; however, it is contemplated that operator could use the module 70 to interact with base 14 as well.

Figure 4A:
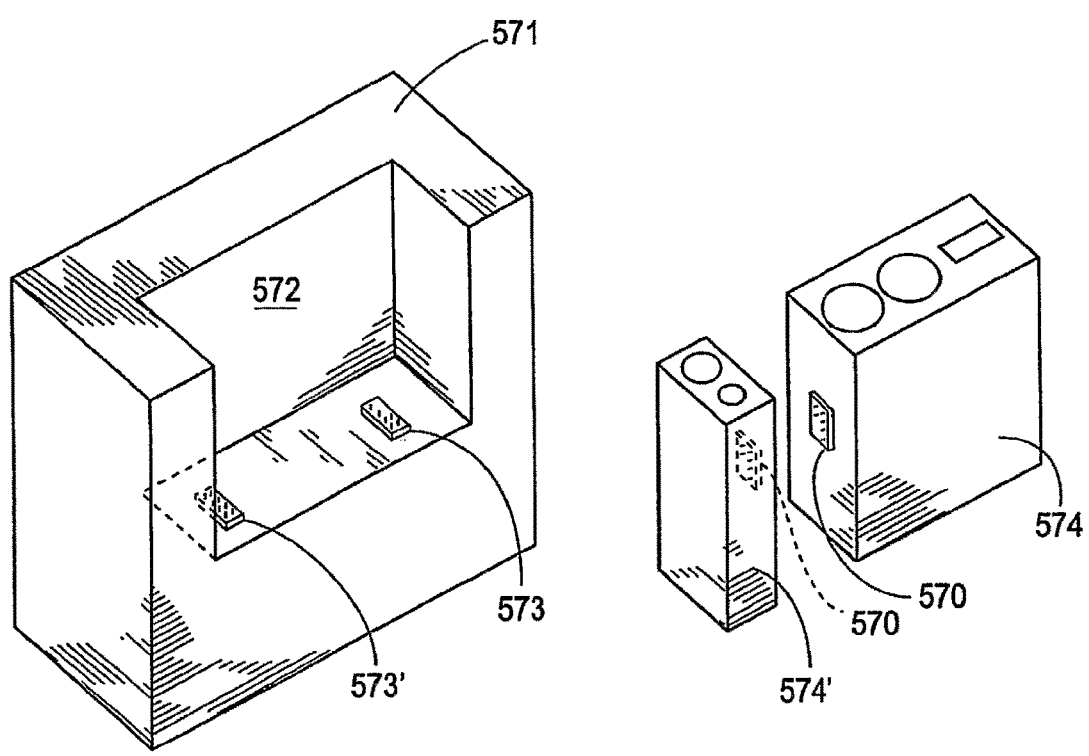
FIG. 4A is a pictorial representation of a multiple patient module storage and attachment assembly in an embodiment of the present teachings.

With reference to FIG. 4A, a pictorial representation of a multiple patient module storage and attachment assembly in an embodiment of the present invention is shown. Pods can come in different sizes generally representing the capability of the pod. For example, smaller pod 574' would provide only the basic features for an external defibrillator, while medium pod 574 would provide several additional features. In the present embodiment, pods 574 and 574' can be docked together in mounting recess or slot 572 contemporaneously. In one embodiment, pod 574 could be latched within mounting slot 572 communicating with base 571 through connector 573. Similarly, pod 574' can be placed within mounting slot 572 contemporaneously with pod 574 and latched in a communicating relationship with base 571 through connector 573'. In another embodiment, pods 574 and 574' could be placed within mounting slot 572 without the need for two base-to-pod connectors 573. Pod 574 and 574' latch together and communicate through connectors 570. Then both pods 574 and 574' are placed within mounting slot 572 and latched in a communicating relationship with base 571 through connector 573. This embodiment not only limits the amount of connectors needed on base 571, but also allows the user to choose the amount of functions the pod can perform. For example, if the user simply needed to perform an ECG, then the user could choose to carry small pod 574'. However, if the emergency situation required additional functions such as monitoring blood pressure in an on-invasive method or a pulse oximeter, then the user would choose to carry medium pod 574'. In addition, if the emergency situation required all of the available pod functions, then pod 574' could be latched together with pod 574 to provide a large pod having all necessary functions. It is also further contemplated connectors 573, 573', and 570 could be most any type of connector such as a USB port, an AC power connector, an RS-232 connector or any other type of connector known to those skilled in the art without departing from the spirit of the invention.

Figure 5:
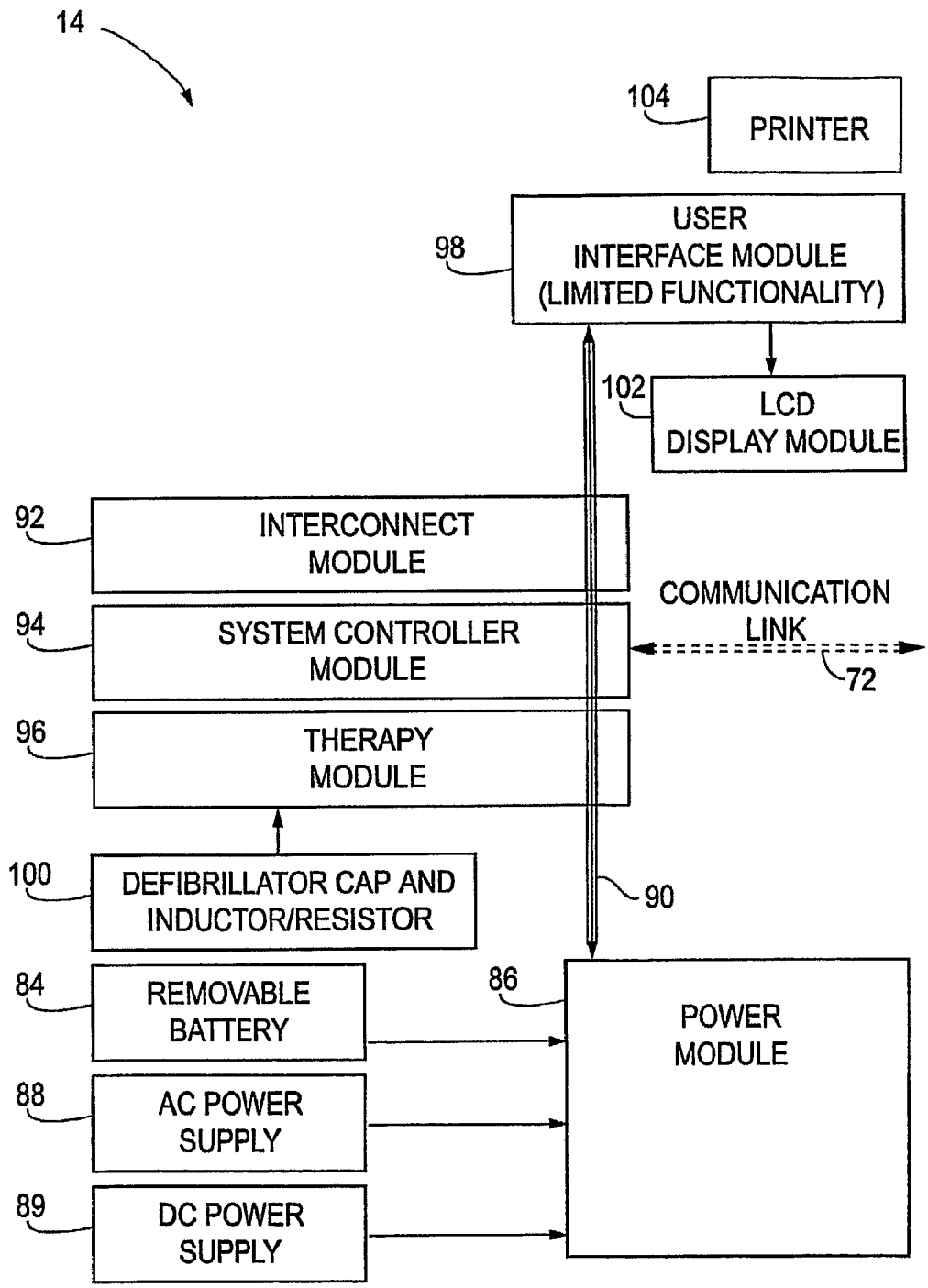
FIG. 5 is a schematic view of a defibrillator/monitor in an embodiment of the present teachings.

With reference to FIG. 5, a schematic view of a defibrillator/monitor in an embodiment of the present teachings is shown. Base 14 is powered by a removable/rechargeable battery 84, which provides power to power module 86. Alternatively, base 14 could be powered by A/C line power 88. Power module 86 processes the incoming power into appropriate powered levels for each of the internal components. Power module 86 also routes the base's power supply through main power and data bus 90 to interconnect module 92, system controller module 94, therapy module 96, and operator interface module 98. Interconnect module 92 is utilized to detect how pod 12 is connected to base 14 (wirelessly, docked, or tethered cable). Similar to system controller module 66 (in FIG. 4), system controller module 94 controls all interaction of all of the base's modules through data bus 90 and interaction with pod 12 through wired or wireless connection communication link 72 or through data bus 90 if pod 12 is connected to base 14. Therapy module 96 synchronizes shocks and pacing pulses to the patient's intrinsic rhythm from data acquired from pod 12. Module 96 administers shocks from voltages via the defibrillation cap 100 and, in turn, administers pacing pulses to a patient. Operator interface module 98 allows the operator to primarily interact with base 14; however, it is contemplated that the operator could use the module 98 to interact with pod 12 as well. LCD module 102 allows the operator to view a patient's monitored parameters. Finally, the operator has the option to print out patient information on a printer 104 (e.g., a 100 mm strip chart printer).

As stated before the pod is a detachable component of the defibrillator. It is generally stored within a receiving portion of the defibrillator but may be detached and carried to the emergency site, where it is used to monitor various medical parameters of the patient. The pod communicates information to the defibrillator either electrically or wirelessly. Typically, electrical communication is used when the pod is stored within the defibrillator and wireless communication is used when the pod is detached from the defibrillator.

When communicating electrically, the defibrillator and pod are connected through electrical connections. In certain embodiments, the electrical connections comprise one or more leads connecting the defibrillator to the pod. In other embodiments, the electrical connections comprise direct electrical contact between the defibrillator and pod. For example, the pod may be stored within the defibrillator in such a way that each of their electrical components is in direct contact with each other. This direct electrical contact can be used for exchanging data or for recharging the pod battery.

When communicating wirelessly, the defibrillator and pod communicate via a wireless link. Typically, wireless communication is used when the pod is detached from the defibrillator. However, wireless communication can also be used when the pod is stored within the receiving portion.

The pod typically includes a display. The display can be used to display information that medical personnel may need while monitoring and/or delivering therapeutic functions to the patient at the emergency site. The display is primarily used for displaying patient information. For example, the display may be used to display current and historical patient data.

Figure 6:
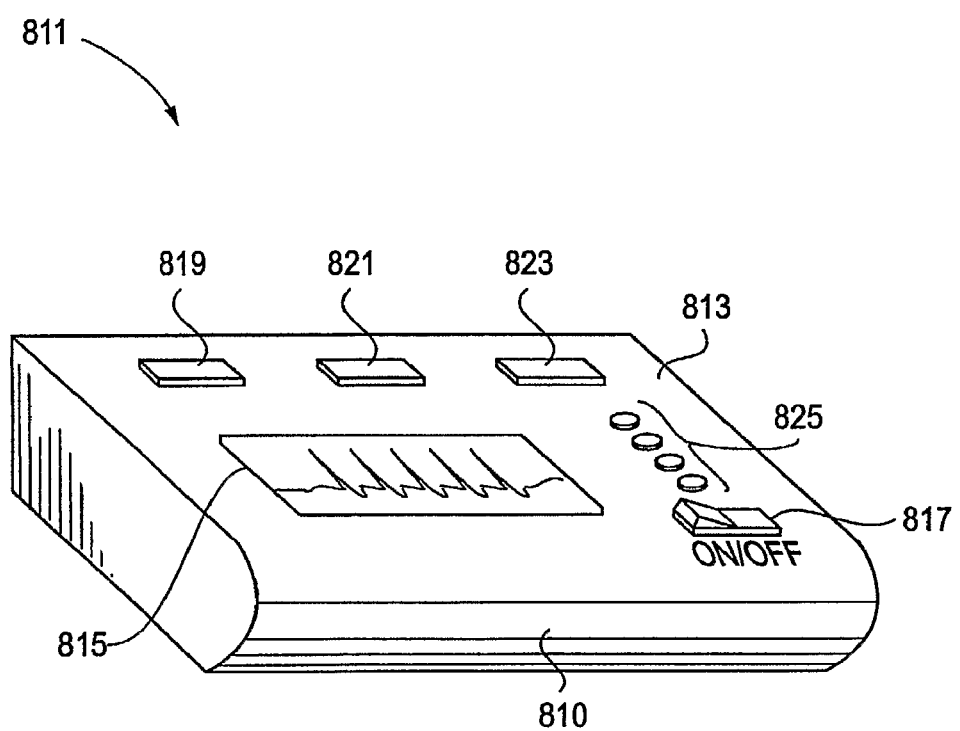
FIG. 6 is a perspective view of a pod and pod display according to one embodiment of the teachings.

With reference to FIG. 6, an illustration of a pod display according to one embodiment of the teachings is shown. In this embodiment, pod 811 has a housing 810 having a small display 813 with a limited user interface. As shown, the pod display 813 includes an ECG monitor 815 for displaying primary waveform information, a control 817 for activation of the pod 811, a control 819, a 12-lead control 821 and a warning signal 823. In certain embodiments, the control 819 is a non-invasive blood pressure (NIBP) control, which allows the medical personnel to initiate a blood pressure reading. Likewise, 12-lead control 821 allows the medical personnel to initiate a 12-lead monitoring session. The warning signal 823 serves to warn of events such as a communication failure between the pod and the defibrillator. Additionally, there are one or more status lights 825 located on the pod display 813. The lights 825, e.g., preferably Light Emitting Diodes (LEDs), are preferably used as indicators for the pod, involving such parameters concerning the battery, the connection quality, the pod location, etc.

Figure 7:
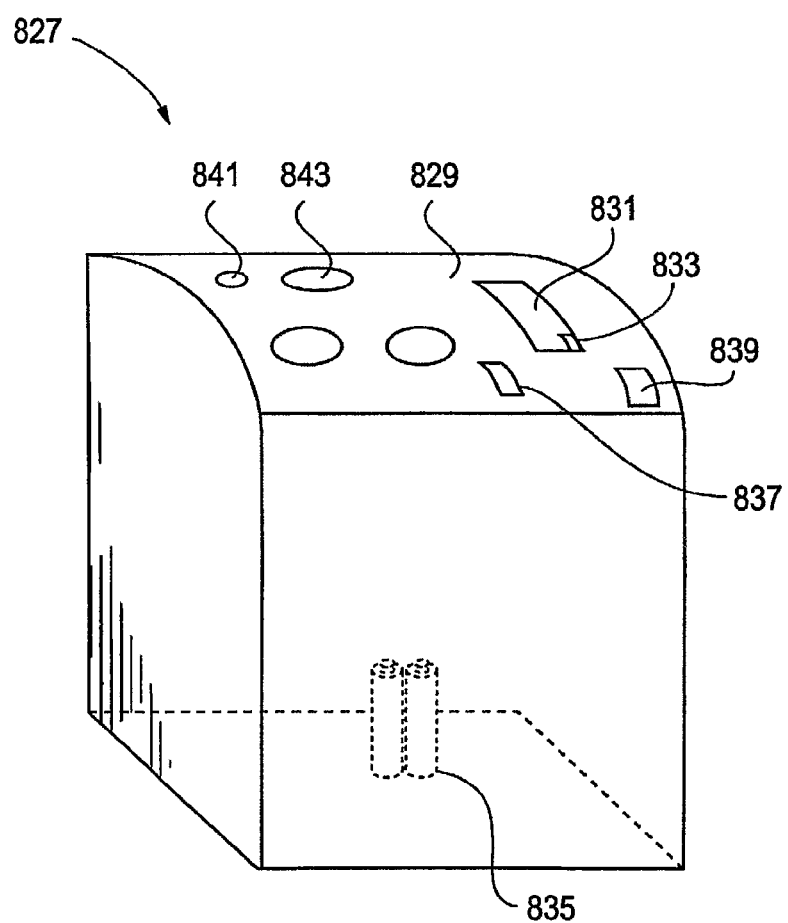
FIG. 7 is a perspective view of a pod and pod display according to one embodiment of the teachings, showing batteries positioned within.

With respect to FIG. 7, an illustration of a pod display according to another embodiment of the teachings is shown. In this embodiment, pod 827 has a pod display 829 including a screen 831 for monitoring various patient parameters, for example monitoring primary waveform information. Screen 831 also contains a battery status indicator 833. Battery status indicator 833 displays the current power level of pod batteries 835. Pod batteries 835 are positioned in electrical contact within pod 827. Pod display of FIG. 7 also includes a serial port 837, a control 839 for powering on and off pod 827, a warning signal 841, and a speaker 843. Warning signal 841 serves to warn of events such as a communication failure between pod 827 and the defibrillator as discussed above. Speaker 843 sounds an alarm along with warning signal 841 to alert the medical personnel of warning events.

In many cases, it is desirable to protect the patient cables connecting the patient and the pod. The leads should remain connected to the patient at the emergency site and also while transporting the patient from the emergency site. Any accidental disconnection of the leads may cause a disruption in the monitoring and/or therapeutic processes.

Figure 8:
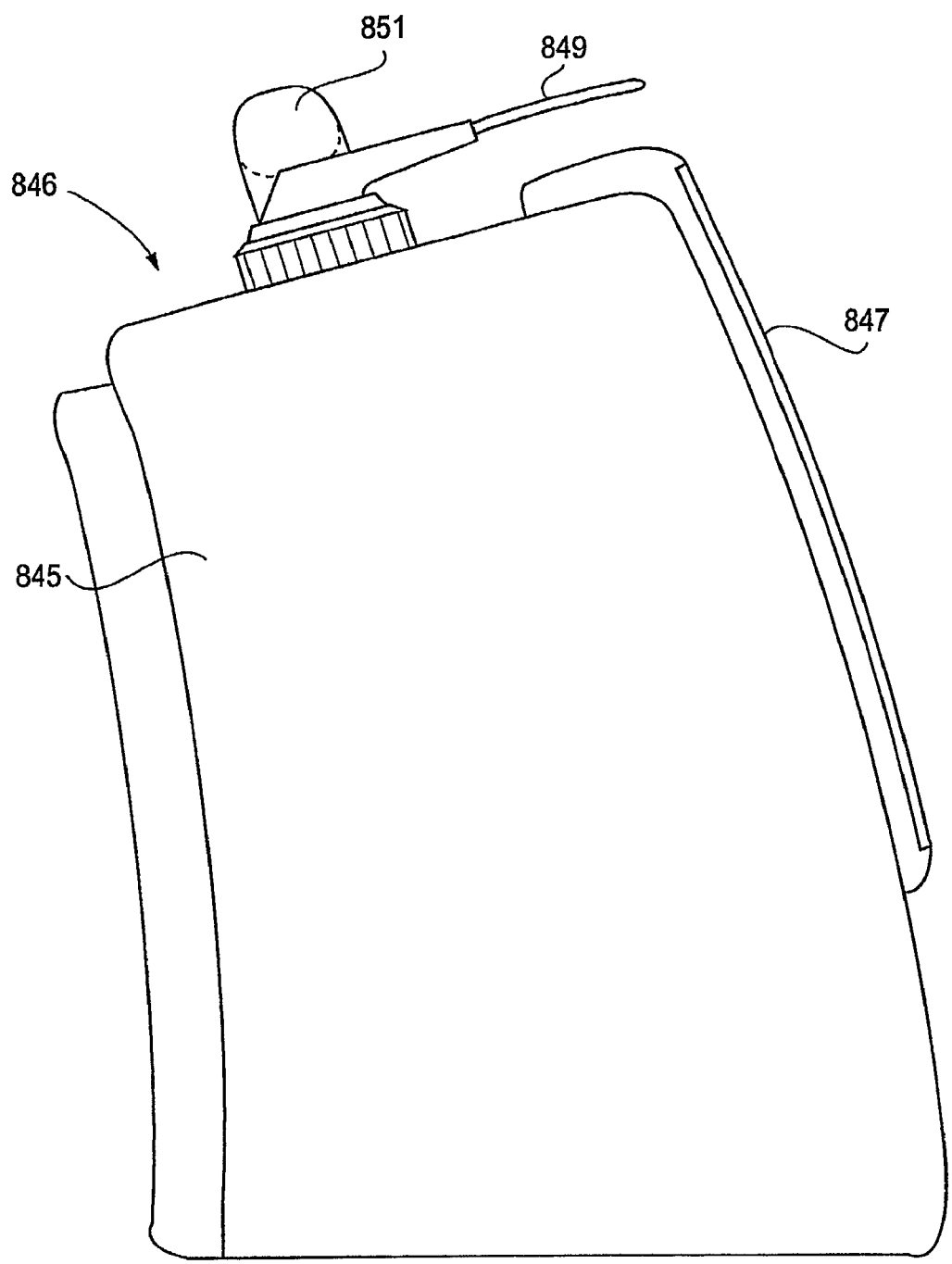
FIG. 8 is a side view of a pod according to one embodiment of the teachings, showing the position of the connectors and handle.

With reference to FIG. 8, a side view of a pod according to one embodiment of the teachings, showing the position of the connectors and handle is shown. In certain embodiments, the pod itself is designed in a manner so if an object accidentally contacts the pod, or if the pod is dropped, the connected leads will be protected. For example, a pod 846 is shown comprising a main unit 845, a display 847, one or more connectors 849 and a carrying handle 851. Connectors 849 are located on the top portion of pod 846 and slightly below carrying handle 851 so if an object contacts the pod from the top, the object will make contact with handle 851 before it contacts connectors 849. Likewise, if the pod is dropped so that the top makes contact with the ground, carrying handle 851 will make contact with the ground, thereby giving some protection to connectors 849 located below.

It is also desirable to ensure that the leads are connected to the patient and the pod in an organized manner. For example, anywhere between 1 to 12 or more leads may be connected to the patient and pod and it would be desirable to easily separate and/or untangle the leads. The present teachings also provides for a lead separator for organizing and separating the patient leads.

Figure 9:
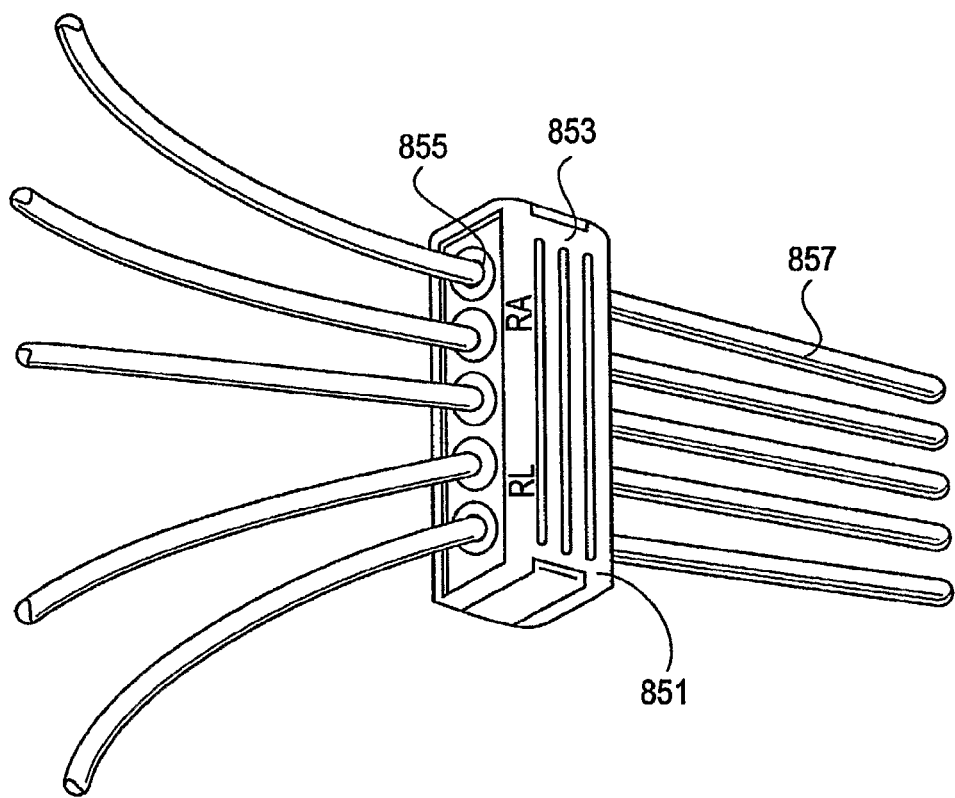
FIG. 9 is a perspective view of a lead separator according to one embodiment of the teachings.

With reference to FIG. 9, an illustration of a lead separator according to an embodiment of the teachings. Lead separator 853 contains holes or apertures 855 for receiving leads 857. When leads 857 are secured within holes 855, lead separator 853 may be slidably moved along the length of leads 857, as opposed to being clamped in one position. As separator 853 slides along the length of leads 857, leads 857 are separated in an organized fashion. Separator 853 can have a top portion 851 and bottom portion 854 which snap together to hold leads 857 within apertures 855.

It is often desirable to have a carrying bag 859 for easily transporting the pod to and from the emergency site. A pod-carrying bag 859 is also desirable for protecting the pod, its connectors, and other components from the outside environment. Thus, the present teachings also provides a carrying bag 859 for carrying the pod. Any suitable carrying bag may be used for carrying the pod.

Figure 10:
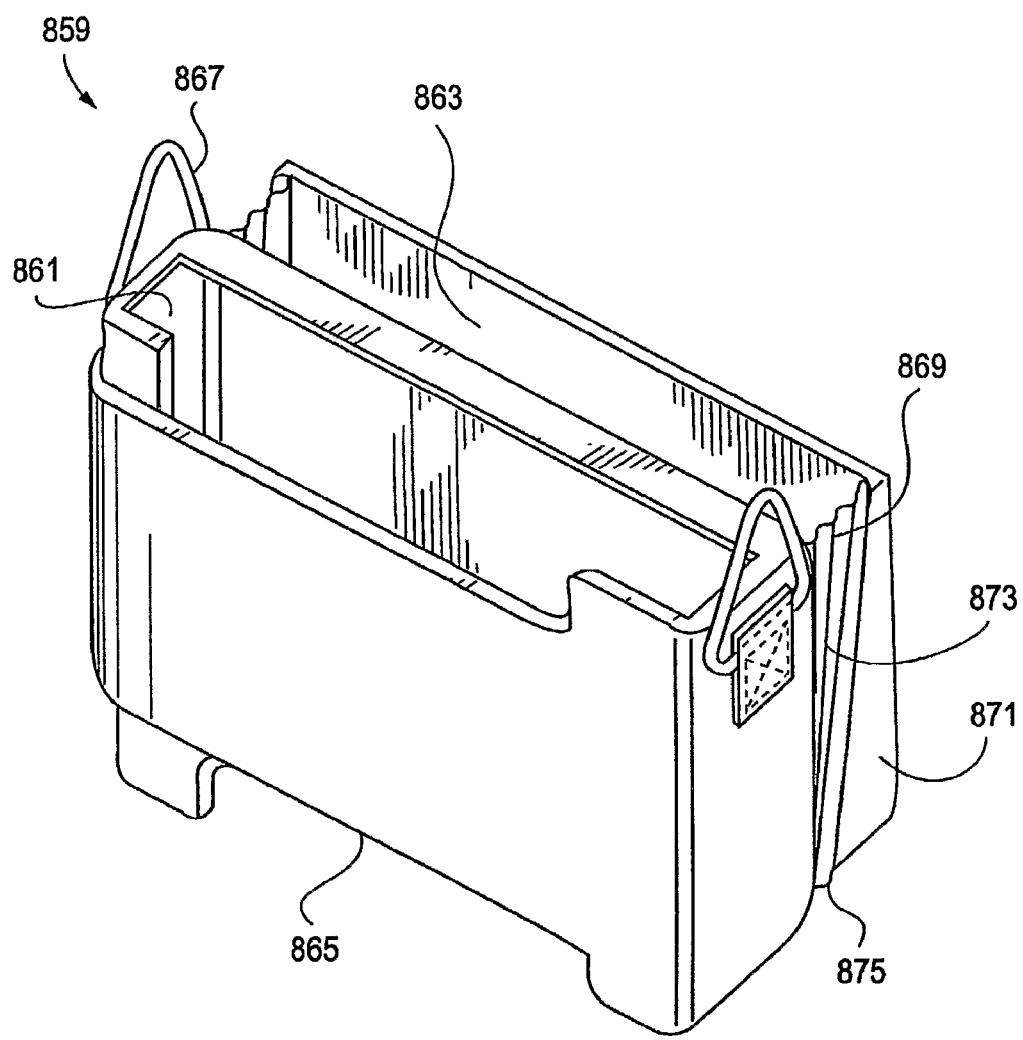
FIG. 10 is a perspective view of a pod carrying bag according to one embodiment of the teachings.
Figure 11:
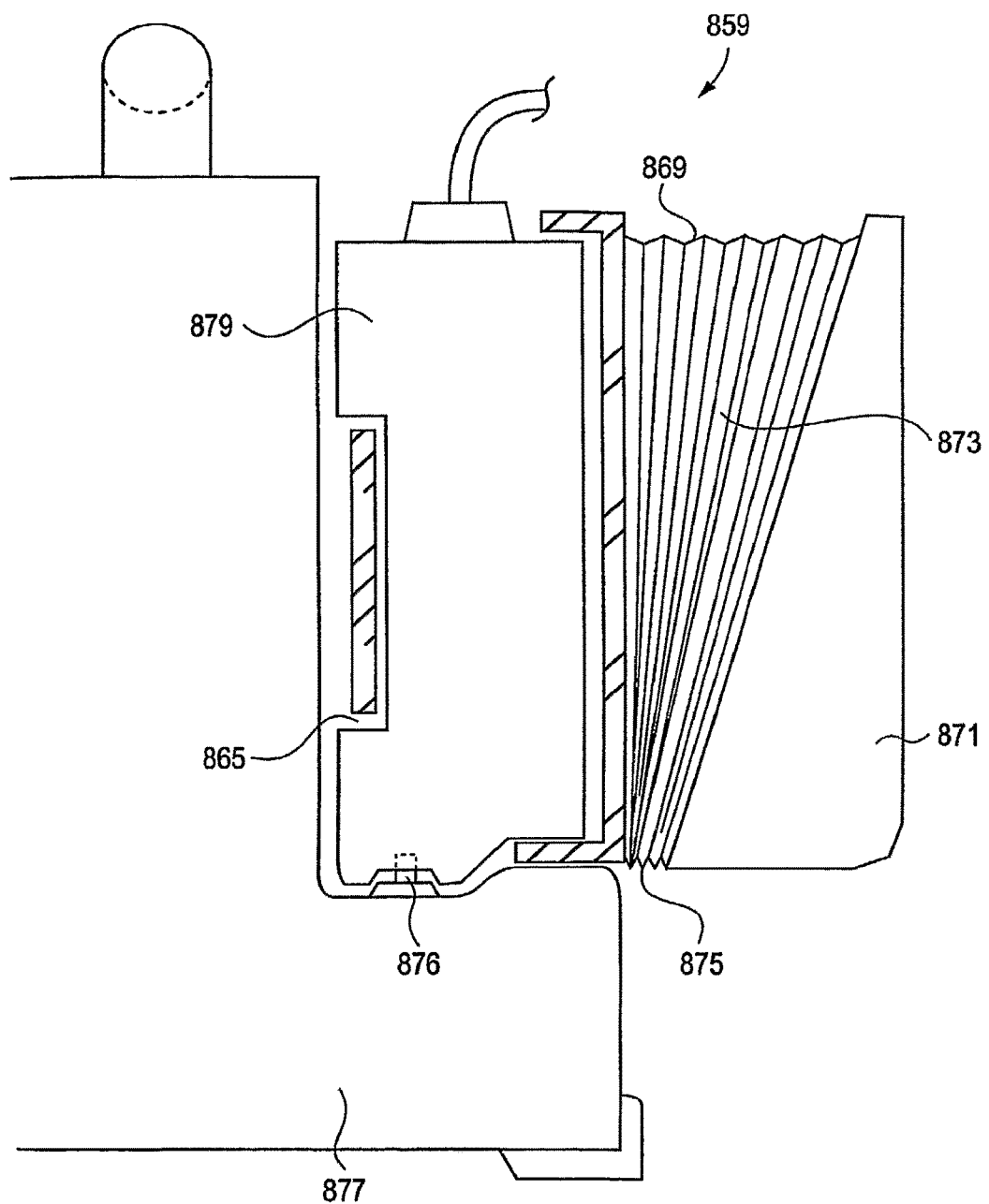
FIG. 11 is a side view of the pod carrying bag displayed in FIG. 5 in a connected position with a defibrillator.

With reference to FIGS. 10 and 11, a perspective view of a pod carrying bag according to one embodiment of the teachings is shown. In this embodiment, carrying bag 859 includes a pod compartment 861 for receiving a pod and a pod component compartment 863 for receiving components of the pod. Pod compartment 861 has a cutout portion 865 so the pod may be positioned in pod compartment 861 so certain of the pod's electrical components are openly accessible through cutout portion 865, such as direct electrical connection 876 between a pod and a base. Further, shoulder strap rings 867 are secured to opposing sides of pod compartment 861 for receiving a shoulder strap.

Component compartment 863 comprises an expandable portion 869 and a formed shell 871. Expandable portion 869 is connected to pod compartment 861 and comprises a plurality of accordion-like folds 873. The accordion-like folds 873 are hinged together at a common hinge 875. A formed shell 871 is connected to the expandable portion 869 at a point furthest from pod compartment 861. Formed shell 871 comprises a durable material and serves to protect the pod components.

With reference to FIG. 11, a side view of the pod-carrying bag displayed in FIG. 10 in a connected position with a defibrillator is shown. A pod 879 and carrying bag 859 may be positioned in electrical contact with a defibrillator 877. When a pod 879 is positioned within carrying bag 859, certain of the pod's electrical components are openly accessible through cutout portion 865. Carrying bag 859 may be positioned upon defibrillator 877 so the pod's exposed electrical components are in direct contact with electrical components of defibrillator 877. This direct electrical contact can be used for exchanging data or for recharging the pod battery.

While an carrying bag has been described in FIGS. 10 and 11, it should be apparent any suitable carrying bag could be used. For example, the carrying bag may include any number of pouches or compartments for storing the pod and pod components. The pouches may also be expandable in design. The pouches may be opened and closed using any suitable mechanism. For example, the pouches may be opened and closed using zippers, Velcro fasteners, or magnetic fasteners. The pouches may also be comprised of several different shapes. The shapes can directly correspond to the shape of the pod itself. Carrying bag 859 may be comprised of any suitable material. In some embodiments, the bag may be comprised of a cleanable material that is flexible, yet sturdy material, such as nylon, plastic, fabric, or any other like materials. In other embodiments, the bag may be comprised of a more rigid shell. A rigid shell is advantageous because it allows for the bag to stand in an upright position rather than sagging or bunching up. A rigid material also serves to protect the pod and module components within carrying bag 859.

A typical pod carrying bag 859 will have means for carrying bag 859. For example, carrying bag 859 may be carried by use of a shoulder strap or by use of padded handgrips. In embodiments, a shoulder strap is used for carrying bag 859. A shoulder strap may also be attached directly to pod 879 itself, without the use of a carrying bag 859.

The shoulder straps may be attached to the carrying bag 859 in any suitable manner. For example, in some embodiments, as the embodiment shown in FIG. 10, the shoulder straps may be attached to carrying bag 859 through the use of shoulder strap rings. In other embodiments, reinforced double stitching and/or reinforcing patches may be used to attach the shoulder strap to the fabric of carrying bag 859. The shoulder strap may be an adjustable strap, so that the user can adjust the strap for a best fit.

Figure 12:
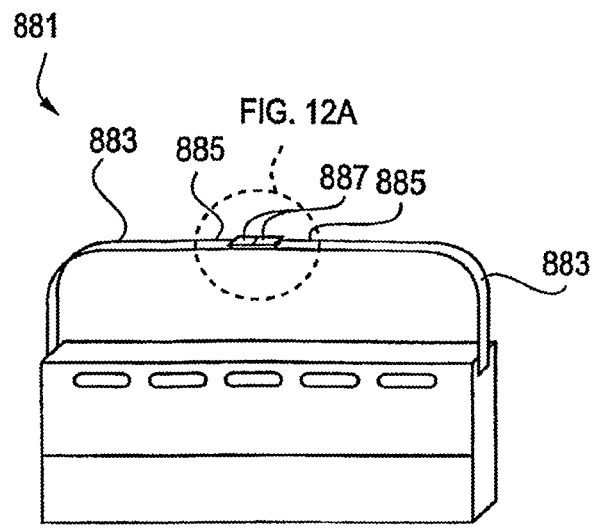
FIG. 12 is a front view of a pod carrying bag having a shoulder strap in accordance with one embodiment of the teachings.
Figure 12A:
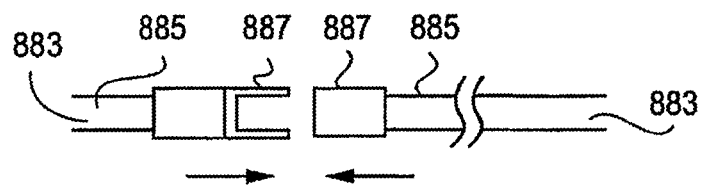
FIG. 12A is a front view close-up of a buckle for a pod carrying bag having a should strap as shown in FIG. 12 in an embodiment of the present teachings.

In embodiments, as in the embodiment shown in FIG. 12, a shoulder strap 881 is provided including two straps 883 attached to the main body of the carrying bag and each having an end 885 with corresponding fasteners 887 secured thereto. It should also be apparent these two straps 883 could be attached to the pod itself, rather than to the carrying bag. Fasteners 887 are used to secure the ends 885 of two straps 883 together, forming a single, connected shoulder strap. Any suitable fastening feature can be used to secure the ends of two straps 883 together. In embodiments, fasteners 887 include quick release buckles.

With the present teachings, it would also be desirable to provide a means for securing the pod to a patient gurney. It is desirable to secure the pod to a gurney for several reasons. For example, it is desirable to secure the pod to a gurney so that medical personnel have easy access to the module and corresponding equipment. In medical emergencies, time is of the essence and it is vitally important to have all necessary medical equipment and supplies, including the pod, readily on hand for use by paramedics, doctors and so on, while the patient is transported to and from an ambulance, emergency room, operating room or intensive care ward. Likewise, it is desirable to secure the pod to a gurney in order to prevent any movement of the pod relative to the patient, which may lead to disconnection of the leads connecting the pod to the patient.

Figure 13:
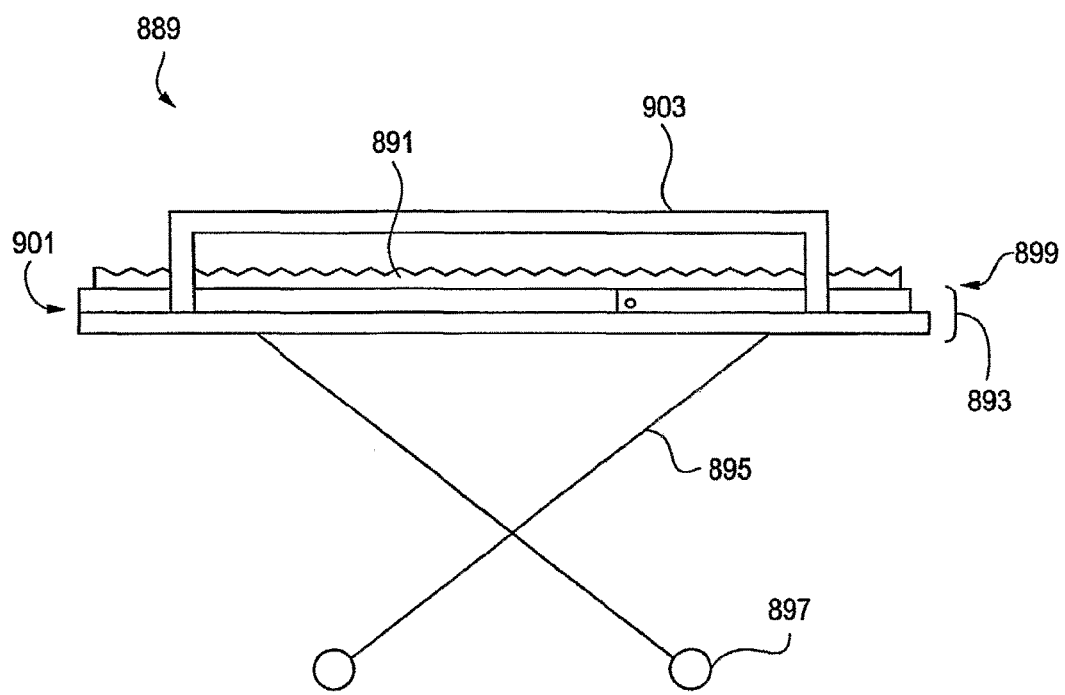
FIG. 13 is a side view of a standard patient gurney.
Figure 14:
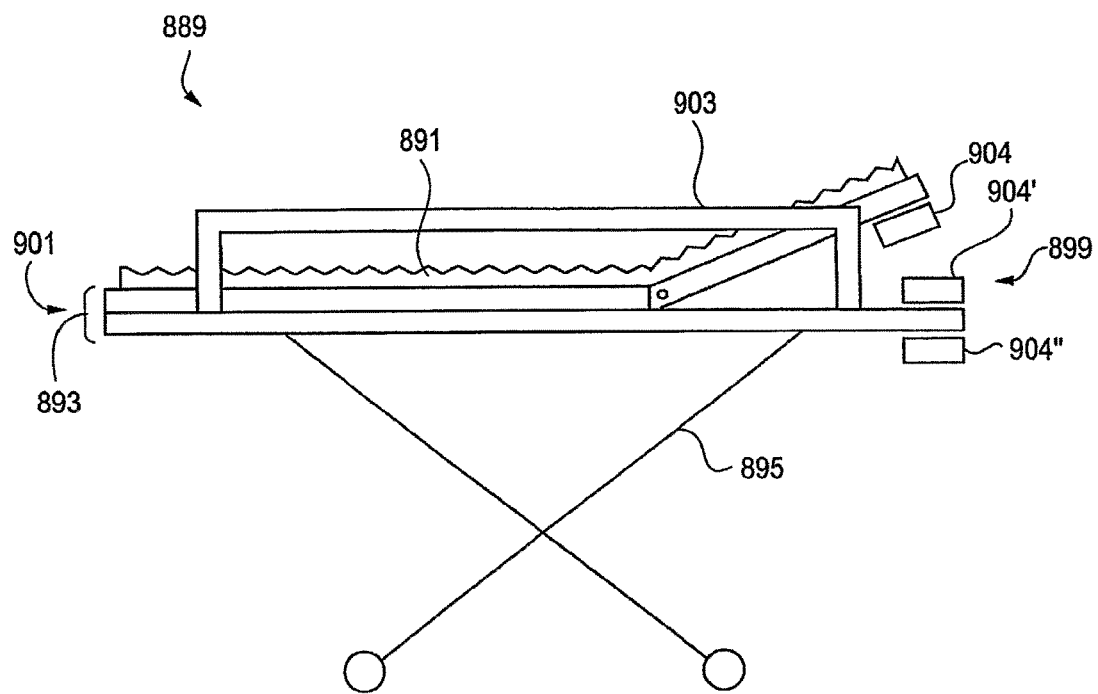
FIG. 14 is side view of a patient gurney adjusted to allow for pod mounting.

As shown in FIG. 13, a typical gurney 889 includes a mattress 891 resting atop and/or fastened to a supporting surface 893. Supporting surface 893 is generally mounted atop an adjustable frame 895. Wheels 897 are typically provided on adjustable frame 895 to allow gurney 889 to be pushed or pulled along the ground. Running between corresponding corners of a front portion 899 and a rear portion 901 of the gurney 889 are two side rails 903 (only one is visibly shown), typically mounted atop the supporting surface 893. In certain preferable embodiments, the gurney 889 is adjustable as illustrated in FIG. 14. The part of the supporting surface 893 on the front portion 899 of the gurney 889 preferably can be raised or lowered. In turn, the patient respiratory region is subsequently elevated, making monitoring therefrom easier to set up and making treatment thereto easier to administer. As such, a pod 904 can be operatively coupled below the raised portion of the supporting surface 893, or a pod 904' can be operatively coupled above the rigid portion of the supporting surface 893, or a pod 904" can be operatively coupled below the rigid portion of the supporting surface 893. Such coupling is preferably provided through the use of appropriate brackets (not shown) which secure the pod to the gurney 899 in these various positions. Alternatively, the pod could likewise be coupled to the rear portion 901 of the gurney 899 when applicable. By being located in any of these positions, the pod is made more accessible for the paramedic (i.e., easier to view and make changes) during monitoring or treatment of the patient.

Figure 15:
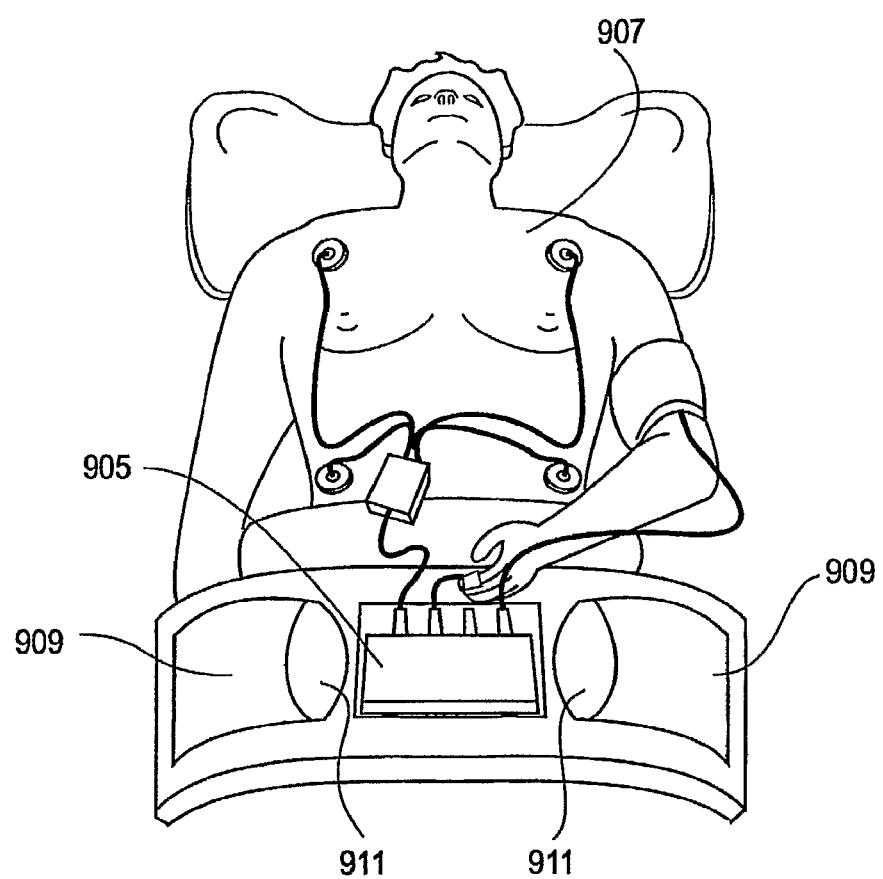
FIG. 15 is an elevated view of a pod positioned on top of a patient.

In some embodiments, the pod can be positioned alongside the patient on the gurney mattress. In other embodiments, the pod can be placed on the patient himself. For example, FIG. 15 shows a pod 905 placed on a patient 907. Pod 905 includes two side flaps 909 attached to opposing sides of pod 905. Side flaps 909 each include an internal pouch 911 for carrying components of pod 905. When pod 905 is not positioned on top of a patient 907, each side flap 909 may be folded over the top of pod 905 so the side flaps 909 overlap one another and so the internal pouches 911 are not visible. The overlapped side flaps 909 may be held together in overlapped position via Velcro strips, snaps, or any other attachment mechanism. In certain embodiments, one side flap may be longer than the other side flap so it can easily overlap the other side flap.

When it is desired to position pod 905 on patient 907, two side flaps 909 are separated and folded downward over the body of patient 907 in a manner as displayed in FIG. 15. When side flaps 909 are in this folded downward position, pod 905 is stabilized on patient 907 and inner pouches 911 are visible.

While it is perfectly suitable to place pod 905 on top of patient 907, it is often desirable (and sometimes necessary) to position pod 905 in proximity to patient 907 but not on top of or along with patient 907 on the gurney mattress, as mentioned above. For example, many ambulance gurneys are relatively compact so they may fit within an ambulance or transport helicopter and allow sufficient room for medical personnel to attend to patient 907 during transport. As a result, there is often not enough room for pod 905 to be placed on the gurney mattress.

In addition to mounting the pod onto the supporting surface 893 of the gurney as described above, the pod may also be positioned about one of the rails of the gurney. In certain embodiments, as in FIG. 16, a shoulder strap secures the pod or pod-carrying bag to a gurney rail. In other embodiments, as in FIG. 16, a holding tray is provided on a gurney rail for holding the pod.

Figure 16:
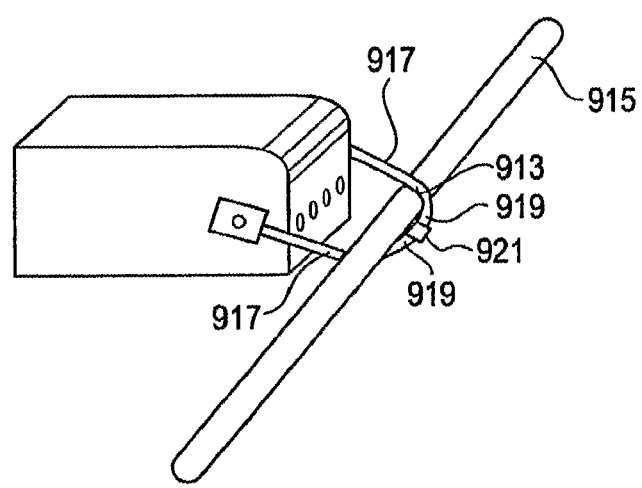
FIG. 16 is a perspective view of a pod shoulder strap secured to a gurney rail.

In FIG. 16, a shoulder strap 913 is provided for securing a pod or pod carrying bag to a gurney rail 915. Like the shoulder strap described in FIG. 12, shoulder strap 913 includes two straps 917 attached to the main body of the carrying bag or pod and each having an end 919 with corresponding fasteners 921, e.g., quick release buckles secured to each end. When it is desired to secure the pod or carrying bag to a gurney rail 915, the paramedic can strap wrap the unconnected straps 917 around a gurney rail 915 and connect them together via the fasteners 921.

Figure 17:
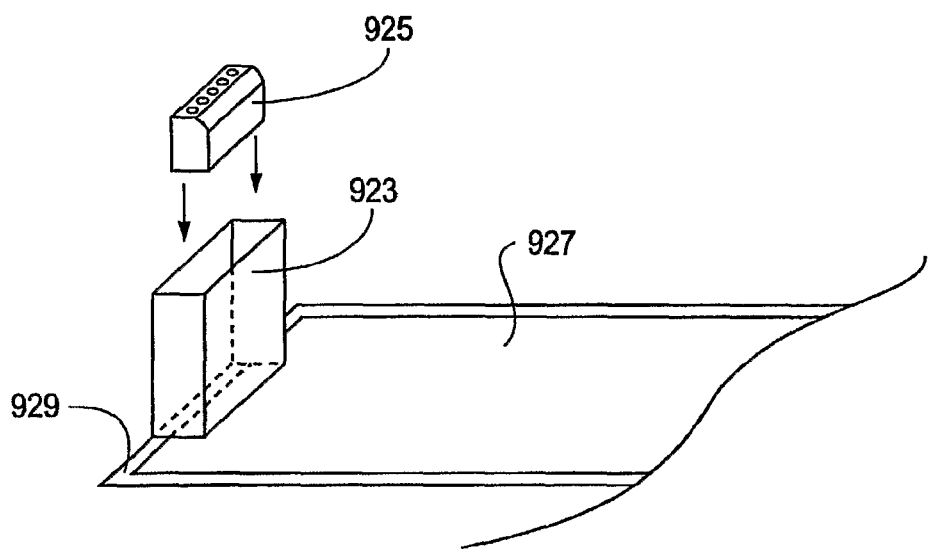
FIG. 17 is a perspective view of a pod holding tray secured to a gurney.

In FIG. 17, a holding tray 923 is provided for securing pod 925 and/or pod carrying bag to a gurney 927 in methods already mentioned or similar methods. Pod holding tray 923 typically includes a tray having dimensions slightly larger than the dimensions of pod 925 and/or pod carrying bag. Any dimensions can be used so long as pod 925 and/or pod-carrying bag is comfortably received within tray 923. In FIG. 17, pod holding tray 923 is secured to a foot rail 929 of the gurney. However, holding tray 923 may also be secured in any suitable position about a gurney, as mentioned above. For example, holding tray 923 can be secured to any of the gurney rails. Additionally, tray 923 can be secured in a position above or beneath the supporting surface of the gurney.

In some embodiments, the holding tray is detachably secured to a gurney so a paramedic may attach tray 923 to a gurney when needed. In other embodiments, the tray is permanently secured to a gurney so no attachment/detachment of the tray is needed. Holding tray 923 can also include support straps for firmly gripping pod 925 and/or pod carrying bag within tray 923. Tray 923 may also be provided with one or more bumper pads around its edges to protect the patient and medical staff from injury if the tray is accidentally bumped into.

One skilled in the art will appreciate that the present teachings can be practiced with embodiments other than those disclosed. The disclosed embodiments are presented for purposes of illustration and not limitation, and the present teachings is limited only by the claims that follow.

The invention claimed is:

1. A patient parameter monitoring pod, comprising:
   a housing;
   a patient lead cable port configured to receive at least a patient lead cable attachable to a patient to collect patient data, the patient data including at least one vital sign;
   a carrying handle extending from a first location on the housing to a second location on the housing, the patient lead cable port disposed between the first and second location, the carrying handle positioned to protect, from any impact, the patient lead cable port and a connection between the at least a patient lead cable and the port when the at least a patient lead cable is attached to the port; and
   a communications module adapted to send the patient data to a defibrillator separate from the housing.

2. The pod of claim 1, wherein the housing includes a pod interconnect connector to connect the pod to another patient parameter monitoring pod.

3. The pod of claim 1, wherein the housing includes visual indicators.

4. The pod of claim 1, further including a lead cable comb separator, the separator holding the lead cables apart from each other.

5. The pod of claim 1, further including a carrying strap connected to one of the pod and a bag.

6. The pod of claim 5, wherein the carrying strap including a quick release buckle permitting the strap to be opened.

7. A patient parameter monitoring pod system, comprising:
   a portable patient monitoring pod having an outer housing, a patient parameter module, and a data port, the patient parameter module configured to be connectable to a patient via lead cables to collect patient data, the patient data including at least one vital sign, the data port being exposed on the housing and adapted to supply the patient data via a direct electrical connection to a defibrillator separate from the pod, the pod including a carrying handle extending from the housing proximate a patient lead cable port that permits connection of the lead cables to the pod, the carrying handle positioned to protect the patient lead cable port and the patient lead cables attached to the port from any impact; and
   a component storage bag having pockets for holding the pod and components of the pod, the storage bag further having openings exposing the data port and permitting passage therethrough of the lead cables when connected to the data port.

8. The pod of claim 7, where the patient data includes one or more of multi-lead ECG data, non-invasive blood pressure data, pulse oximeter data, capnography and respiratory data, invasive blood pressure readings, and patient temperature data.

9. The pod of claim 7, wherein the housing supports a display area to visually display the patient data.

10. The pod of claim 7, wherein the housing includes a pod interconnect connector to connect the pod to another patient parameter monitoring pod.

11. The pod of claim 7, wherein the housing includes visual indicators.

12. The pod of claim 7, further including a lead cable comb separator, the separator holding the lead cables apart from each other.

* * * * *